(12) United States Patent
Kane et al.

(10) Patent No.: US 10,327,833 B2
(45) Date of Patent: Jun. 25, 2019

(54) ELECTROSURGICAL SWITCH ASSEMBLY AND RELATED SYSTEMS AND METHODS

(71) Applicant: TDM SURGITECH INC., Palm Harbor, FL (US)

(72) Inventors: Mark Kane, Campbell, CA (US); Paul J Weber, Queenstown (NZ)

(73) Assignee: TDM Surgitech, Inc., Palm Harbor, FL (US)

(*) Notice: Subject to any disclaimer, the term of this patent is extended or adjusted under 35 U.S.C. 154(b) by 392 days.

(21) Appl. No.: 14/752,946

(22) Filed: Jun. 28, 2015

(65) Prior Publication Data

US 2016/0278840 A1  Sep. 29, 2016

Related U.S. Application Data

(60) Provisional application No. 62/137,806, filed on Mar. 24, 2015.

(51) Int. Cl.
  *A61B 18/12* (2006.01)
  *A61B 18/14* (2006.01)
  *A61B 18/00* (2006.01)

(52) U.S. Cl.
  CPC ...... *A61B 18/1206* (2013.01); *A61B 18/1482* (2013.01); *A61B 2018/00607* (2013.01); *A61B 2018/00791* (2013.01); *A61B 2018/00815* (2013.01); *A61B 2018/00821* (2013.01); *A61B 2018/00922* (2013.01); *A61B 2018/124* (2013.01); *A61B 2018/126* (2013.01);
  (Continued)

(58) Field of Classification Search
  CPC .. A61B 2018/00922; A61B 2018/1467; A61B 2018/00607; A61B 2018/124; A61B 18/1206; A61B 18/1482; A61B 2018/1253; A61B 2018/126; A61B 2018/00791; A61B 2018/00815; A61B 2018/00821; H01H 9/30; H01H 9/38; H01H 9/383; H01H 9/386; H01H 33/045
  See application file for complete search history.

(56) References Cited

U.S. PATENT DOCUMENTS 4,655,215 A  4/1987 Pike
6,113,596 A  9/2000 Hooven
(Continued)

*Primary Examiner* — Jaymi E Della
*Assistant Examiner* — Sean W Collins
(74) *Attorney, Agent, or Firm* — Matthew D. Thayne; Thayne and Davis LLC

(57) ABSTRACT

Switches for electrosurgical devices comprising a plurality of electrode sets and related devices, systems, and methods. In some embodiments, a first electrode set may be configured to deliver CUT radiofrequency energy and a second electrode set configured to deliver COAG radiofrequency energy. A switch assembly may be configured to allow for selection between at least three modes, the at least three modes comprising a first, neutral mode, in which the electrosurgical device is configured such that no radiofrequency energy is delivered to either the first electrode set or the second electrode set, a second, CUT mode, in which the electrosurgical device is configured such that CUT radiofrequency energy may be delivered to the first electrode set through the switch assembly, and a third, COAG mode, in which the electrosurgical device is configured such that COAG radiofrequency energy may be delivered to the second electrode set through the switch assembly.

23 Claims, 16 Drawing Sheets

(52) U.S. Cl.
CPC ............... *A61B 2018/1253* (2013.01); *A61B 2018/1467* (2013.01)

(56) References Cited

U.S. PATENT DOCUMENTS

| | | |
|---|---|---|
| 6,203,540 B1 | 3/2001 | Weber |
| 6,391,023 B1 | 5/2002 | Weber |
| 6,432,101 B1 | 8/2002 | Weber |
| 6,440,121 B1 | 8/2002 | Weber |
| 6,974,450 B2 | 12/2005 | Weber |
| 7,494,488 B2 | 2/2009 | Weber |
| 7,674,261 B2 | 3/2010 | Garito |
| 7,842,033 B2 | 11/2010 | Isaacson |
| 8,932,280 B2 | 1/2015 | Isaacson |
| 2005/0113824 A1* | 5/2005 | Sartor ............... A61B 18/1402 606/42 |
| 2007/0016187 A1* | 1/2007 | Weinberg ............ A61B 18/14 606/42 |
| 2008/0004619 A1 | 1/2008 | Malis |
| 2009/0076504 A1* | 3/2009 | Schnitzler ......... A61B 18/1402 606/45 |
| 2009/0259223 A1 | 10/2009 | Eggers |
| 2011/0144729 A1* | 6/2011 | Weber ............... A61B 18/1402 607/99 |
| 2013/0006239 A1* | 1/2013 | Pikramenos ....... A61B 18/1233 606/41 |
| 2013/0338652 A1* | 12/2013 | Weber .................. A61B 18/14 606/13 |
| 2014/0018795 A1* | 1/2014 | Shilev ............... A61B 18/1402 606/41 |
| 2014/0066927 A1 | 3/2014 | Brustad |
| 2014/0364844 A1 | 12/2014 | Van Wyk |

\* cited by examiner

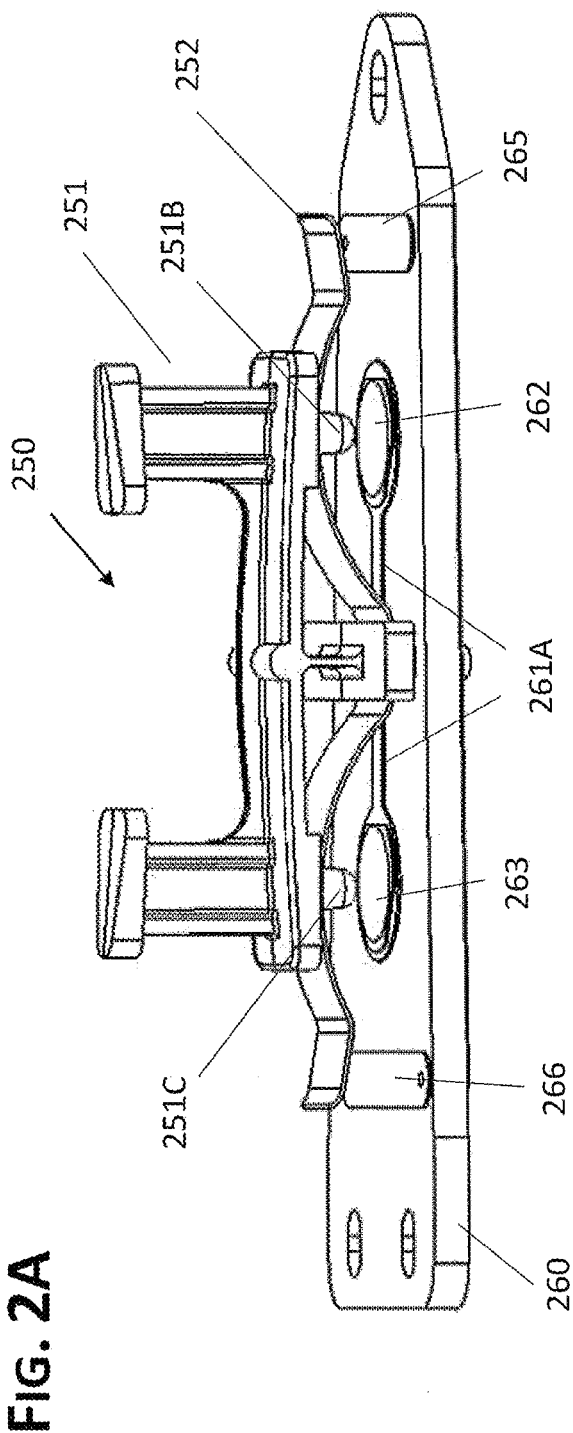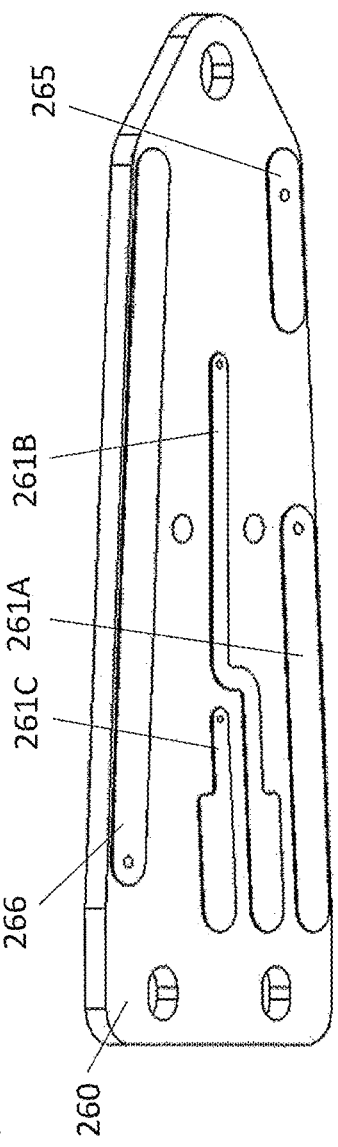
FIG. 2A
FIG. 2B

FIG. 3A
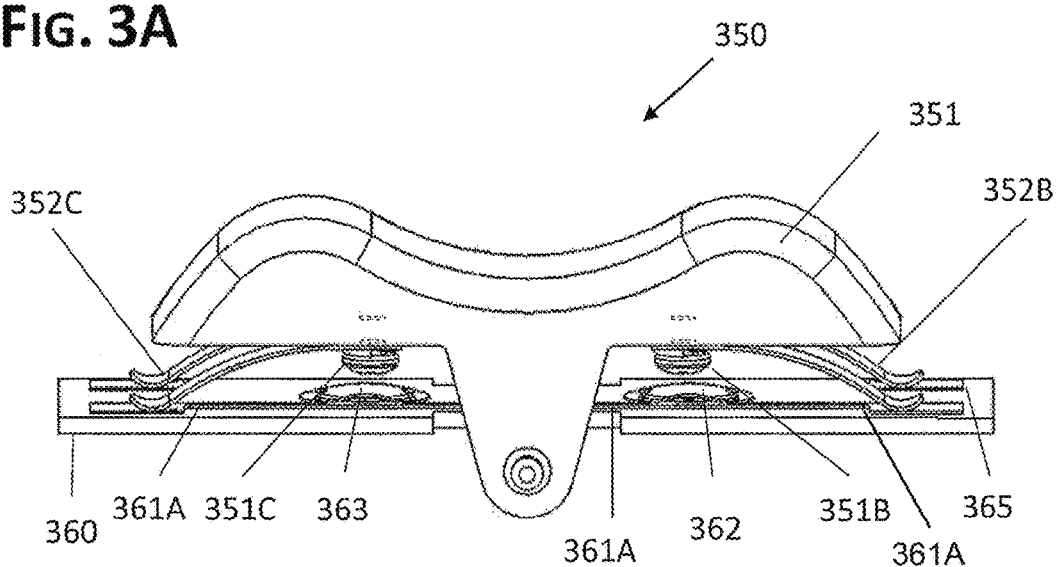
FIG. 3B
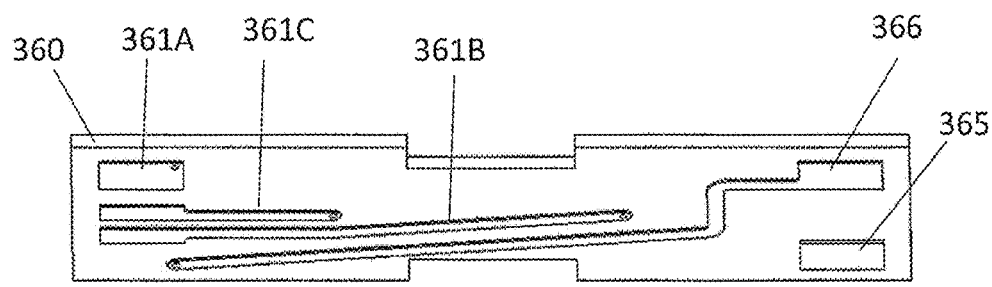
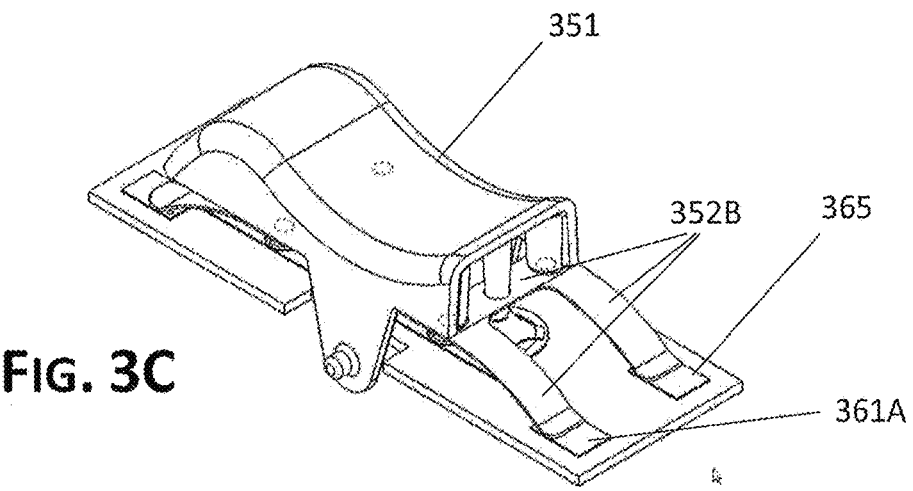
FIG. 3C

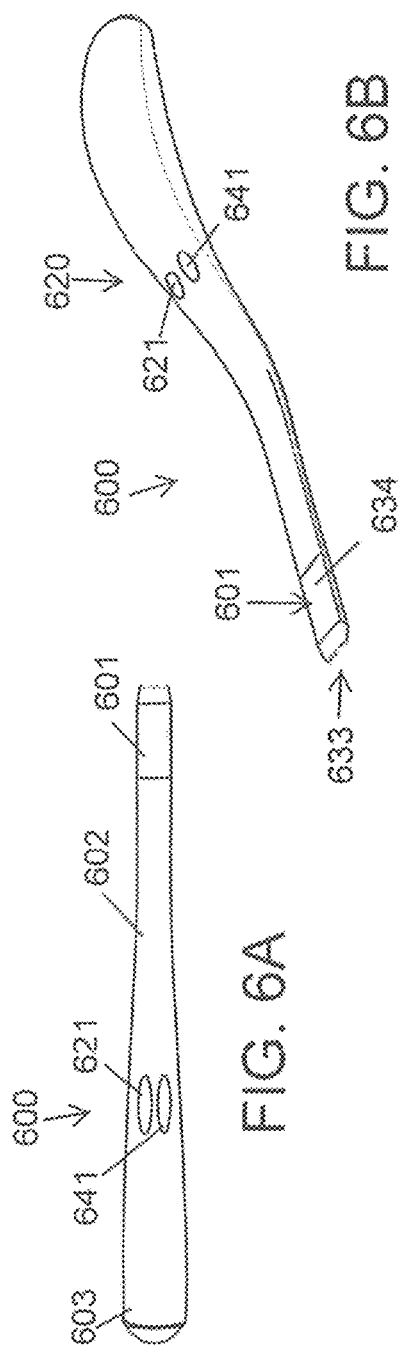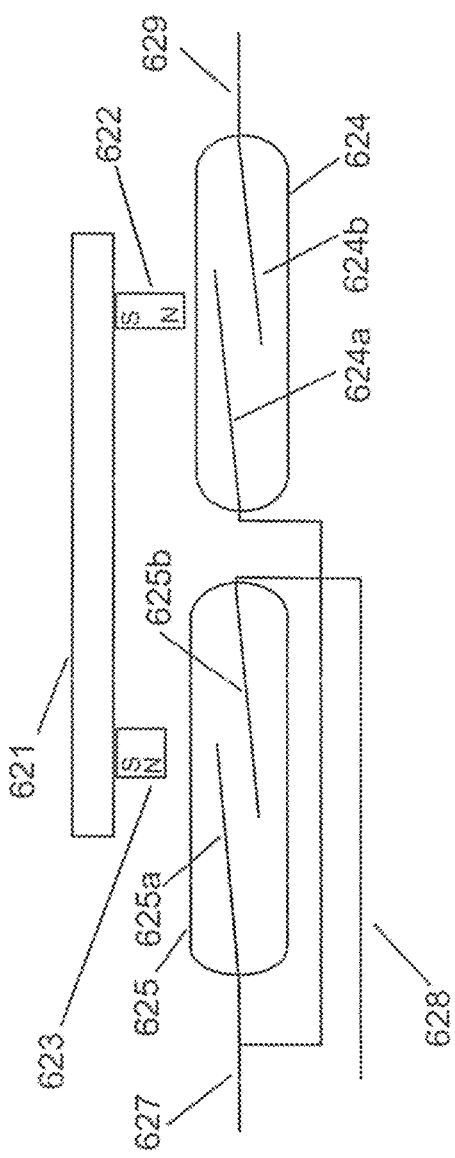

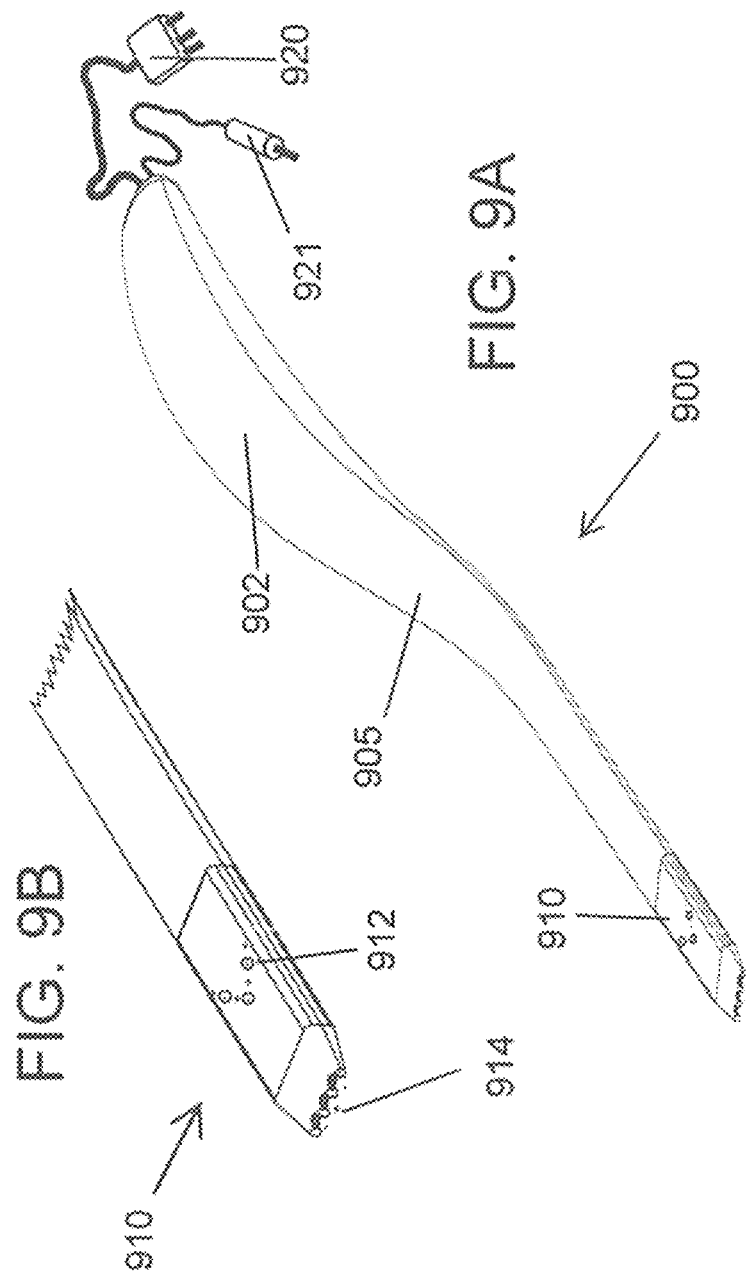

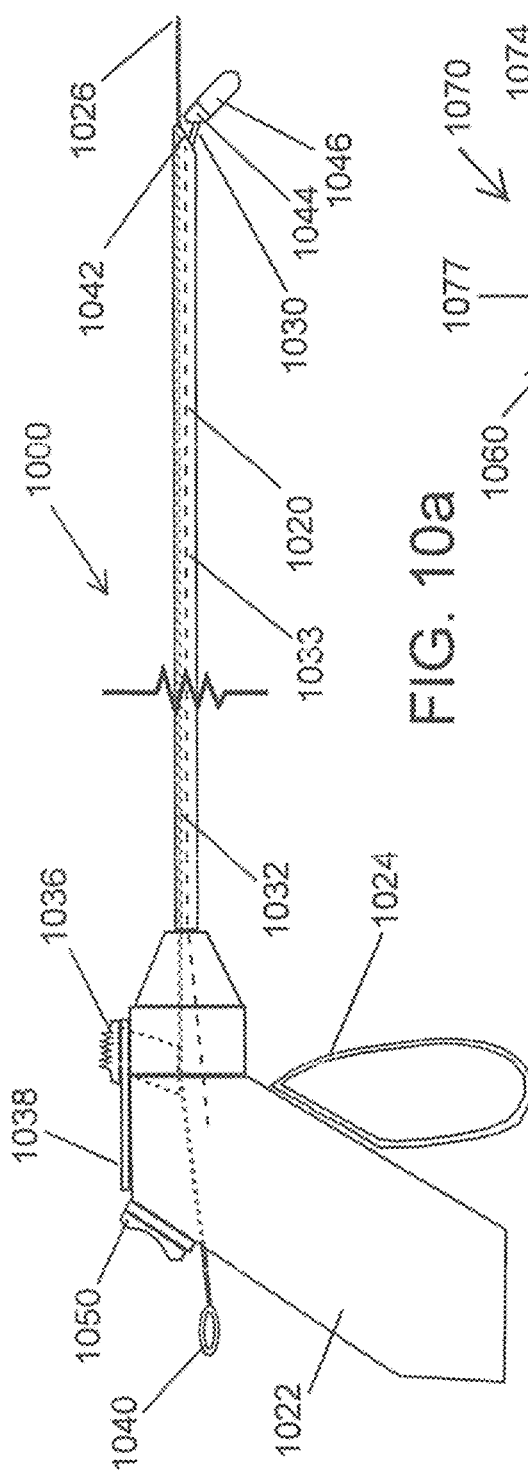
FIG. 10a
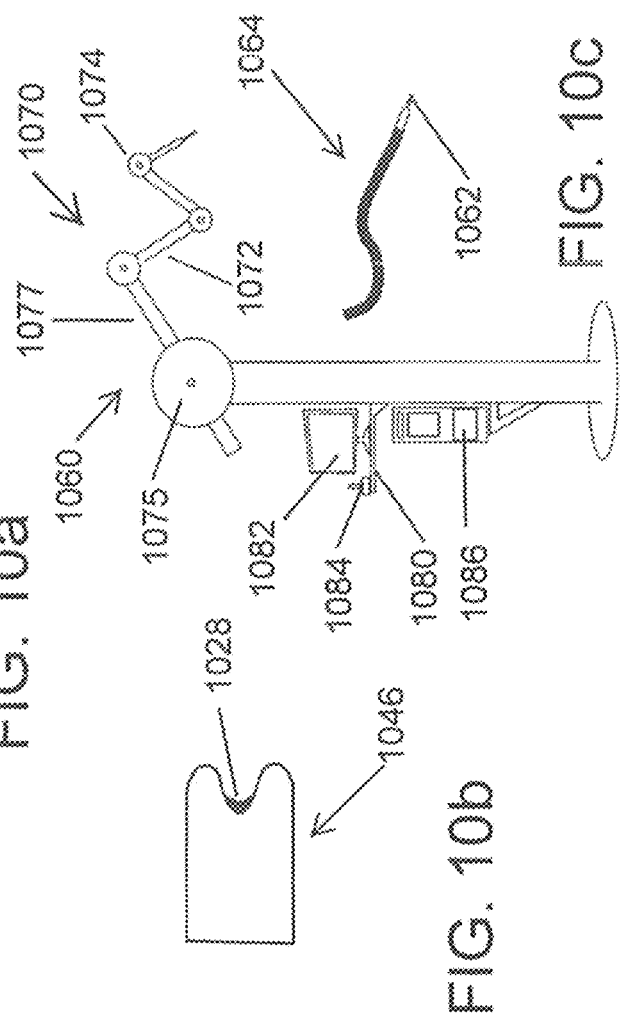
FIG. 10b
FIG. 10c

ELECTROSURGICAL SWITCH ASSEMBLY AND RELATED SYSTEMS AND METHODS

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 2A is a side perspective view of a switch assembly according to one embodiment.

FIG. 2B is a lower perspective view of the switch assembly of FIG. 2A.

FIG. 3A is a side perspective view of another embodiment of a switch assembly.

FIG. 3B is a lower perspective view of the switch assembly of FIG. 3A.

FIG. 3C is a perspective view of switch assembly with cutaway view of a spring component.

FIG. 6A is an upper plan view of a TDM comprising still another embodiment of a switch assembly.

FIG. 6B is a perspective view of the TDM of FIG. 6A.

FIG. 6C is a schematic diagram illustrating one of two actuators of the switch assembly of FIGS. 6A and 6B.

FIG. 9A is a perspective view of another embodiment of a bipolar TDM.

FIG. 9B is a close-up view of a tip of the bipolar TDM of FIG. 9A.

FIG. 10A is a side elevation view of an embodiment of a laparoscopic surgical instrument comprising a TDM tip and a spot coagulator.

FIG. 10B is a close-up view of the TDM tip of the surgical instrument of FIG. 10A.

FIG. 10C illustrates an embodiment of a robotic surgery system comprising a flexible shaft and a TDM tip.

DETAILED DESCRIPTION

Figure 1A:
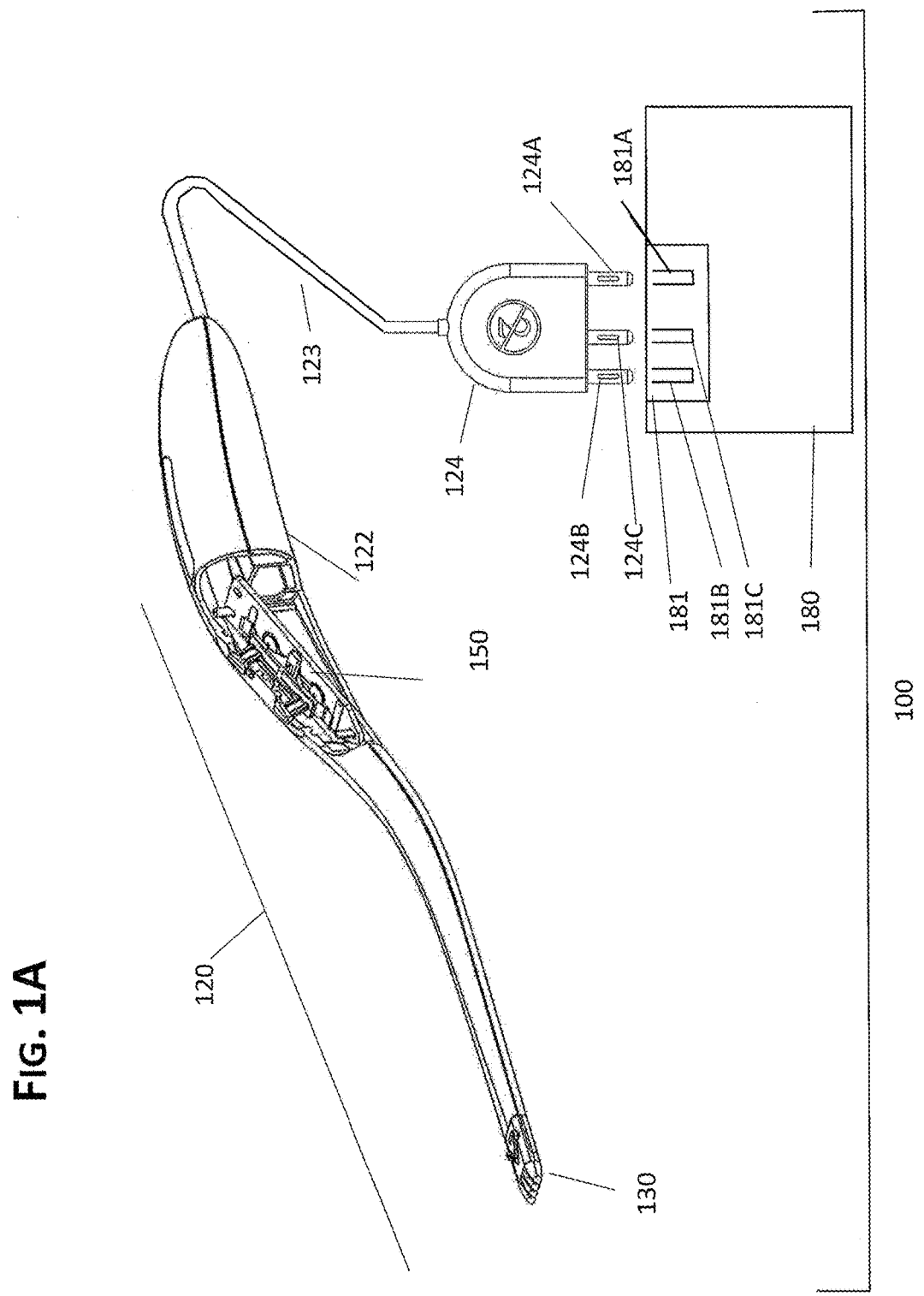
FIG. 1A is a perspective view of the Tissue Dissector and Modifier and the electrosurgical system thereto.

Electrosurgery was invented around 1926 by William T. Bovie and is commonly used in surgery today for dissection and coagulation of tissues using different energy waveforms from the radiofrequency (RF) spectrum.

An electrosurgical system is comprised of multiple components. A first electrosurgical system component may comprise the electrosurgical generator (ESG) that connects into an electrical power outlet and converts electrical energy to various RF energy waveforms. An incomplete list of examples of ESGs include Covidien's Valleylab Force series or Bovie Medical Corporation's ICON GP.

A second electrosurgical system component may comprise a means for delivering RF energy from an ESG to patient tissues (an "energy application means"). According to IEC-60601-1, this component may also be defined as an "Applied Part" as this portion of the system is 'applied' to the patient. Examples of energy application means include, for example, electrosurgical pencils that may contain two sub-components: (1) the 'Handpiece' sub-component that may be held in the surgeon's hand, connects to the ESG, may permit surgeon control of one or more RF energies via myriad types of switching mechanisms, and may contain a retention mechanism for (2) various interchangeable metal electrodes that may come in direct or near direct patient contact depending upon the desired therapeutic effect. Another example of an energy application means is a Tissue Dissection and Modification Wand ("TDM"), which is discussed in greater detail below A third system component that is typically utilized in monopolar systems, not bipolar systems, may be the dispersive electrode (or "return pad") that is attached to the patient and connects to the ESG thus permitting the RF source circuit to be completed; this creates a return path for the RF energy to the ESG preventing patient burns at the return point.

Many ESGs have been designed to operate in at least two modes: the "CUT Mode" and the "COAG Mode".

The COAG Mode delivers an RF waveform through the Handpiece to the electrode tip that desiccates tissues in the immediate vicinity of the tip containing liquid thus promoting a coagulation or bleeding control effect. Some COAG waveforms require electrode contact with the patient while others require the electrode to be nearby the tissue in order to "spray" the current to nearby tissues. These waveforms require very high currents and voltages, for example, the Bovie ICON GP ESG in its instructions for use state the following (in Watts (peak to peak) and Volts): Pinpoint mode, 120 W, 4000V; Spray mode, 120 W, 7000V.

The primary purpose of the CUT Mode is to electrically cut or sever tissue by delivering an RF waveform that electrically arcs from the electrode. As this cutting/arcing waveform is not designed to control bleeding, ESG designers developed the "blended cut" waveform that is one waveform that changes amplitude and frequency and repetition-rate so that it provides a cutting effect as well as a coagulation effect. This Cut/Blend RF Waveform requires very high currents and voltages, for example, the Bovie ICON GP ESG in its instructions for use state the following (in Watts (eak to peak) and Volts): Blend 3, 200 W at 2700V. As used herein, the term CUT Mode is intended to be used in its broadest sense to include all possible 'blend' modes that may be available from an ESG.

Manufacturers have designed 3 or more locations in electrosurgical systems for surgeons to activate and/or choose the desired RF waveform. First, at the ESG user interface panel, an assistant may set the desired RF waveform, the wattage, and may activate the chosen waveform on the surgeon's command. Second, surgeons may activate the CUT or COAG Modes pre-set at the ESG user interface via a foot switch. Third, surgeons may activate CUT or COAG Mode via a switch in the Handpiece of the Applied Part and on some models may adjust output wattages on the Handpiece.

Many electrosurgical systems activated at Handpieces and foot switches are designed with 3 circuits. In some ESG models, Applied Parts with 3-pinned plugs connect into a receptacle on the ESG. Circuit 1 may be called the RF source circuit ("Circuit 1/RF Source Circuit") that carries the chosen RF waveform to the electrode(s); this is typically the pin on a standard 3-ping electrosurgical plug that is separate from the other two pins.

The other two pins comprise the second and third circuits that are low voltage signal circuits that are closed when the surgeon (A) chooses the CUT Mode by activating the CUT aspect of the switch (frequently via button or rocker switches) or (B) chooses the COAG Mode by activating the COAG aspect of the switch. Herein, these two circuits will be referred to as Circuit 2/CUT Mode Signal Circuit and Circuit 3/COAG Mode Signal Circuit. Both signal circuits are powered by various means, depending upon the manufacturer, including supplying a low voltage current from the RF Source line.

Many Applied Parts of electrosurgical systems having monopolar outputs are only comprised of one electrode (in or attached to the Applied Part/Handpiece) that carries either the desired cutting and coagulation RF waveforms. Thus, it may be acceptable for such systems to utilize the same electrode or electrodes for both the cutting and coagulation RF waveforms. However, the Tissue Dissection and Modification Wand ("TDM"), an Applied Part or energy application means described further herein, utilizes 2 or more separate and distinct electrodes that are components in its distal tip. In some preferred embodiments, one or more Cutting Electrodes and one or more Coagulation Electrodes, which may comprise one or more Energy Window Electrodes, may be built into the TDM's distal tip. Because of the high voltages and waveforms' tendency to arc and the requirement to carry each waveform to a particular electrode, a unique means for switching between the cutting and coagulation RF waveforms (a "switching means") may be required to operate the TDM effectively and safely. Some embodiments disclosed herein may therefore comprise a unique switch design to be employed in the TDM's handle or at any location along the wiring of the handle leading to the ESG.

The TDM has myriad uses and configurations some of which are described in the following: U.S. Pat. No. 6,203,540 titled "Ultrasound and Laser Face-Lift and Bulbous Lysing Device," U.S. Pat. No. 6,391,023 titled "Thermal Radiation Facelift Device," U.S. Pat. No. 6,432,101 titled "Surgical Device for Performing Face-Lifting Using Electromagnetic Radiation," U.S. Pat. No. 6,440,121 titled "Surgical Device For Performing Face-Lifting Surgery Using Radiofrequency Energy," U.S. Pat. No. 6,974,450 titled "Face-Lifting Device," and U.S. Pat. No. 7,494,488 titled "Facial Tissue Strengthening and Tightening Device and Methods. Each of the patents referenced above is hereby incorporated herein by specific reference in its entirety. It has recently been discovered that TDM devices may be utilized many other surgical interventions as well.

Unique to TDM is that it contains at least two separate and distinct electrodes. The Cutting Electrode may be exposed at one or more segments or elements (lysing segments or other lysing elements, for example), each recessed between two bulbous protrusions and designed to deploy the cut or Cut/Blend Waveforms generated during the ESG's CUT Mode. The Coagulation Electrode(s) in such devices may comprise Energy Window Electrode(s), and may terminate at one or more locations on one or more energy windows on the various faces of the TDM (on a top surface in certain preferred embodiments) and may be designed to deploy the coagulation energy waveform produced during the ESG's COAG mode. The term "'modifying" in this context may refer to or may encompass application of energy to tissue using one or more lysing segments or lysing elements of a TDM. In some embodiments the lysing elements used to deliver the CUT or BLEND energy may comprise lysing segments. The term "modifying" in this context may also refer to application of energy to tissue by way of an energy window as described herein.

The TDM may therefore be required to operate with very high voltages and conduct currents in very small and confined spaces. As such, the issue to overcome is that during the activation of either modality (CUT or COAG Modes), one switch end will be connected to a high voltage RF point. High voltage RF energy has potentially dangerous characteristics that must be bridled. First, voltages are high, typically 2000V to 4000V. Thus, any errant current could harm the patient, the user, and/or the equipment internally. Second, RF energy has characteristics that can generate sparks in gaps if not properly isolated. This could immediately damage the device making it unsafe for use, or it could gradually degrade over repeated activations making the device unsafe for use. Finally, the circuitry and switching mechanism must fit in a very small space, in many cases in the space-limited Handpiece.

For the TDM to function safely and effectively with 1-source/2-signal ESG systems, it may be desirable to provide a novel switch or switching assembly (A) when the CUT Mode is activated at the switch by the surgeon and/or to call for Cut/Blend RF Waveform(s) to be created at the ESG and carried through the conductive means to the Cutting Electrode and (B) when the COAG Mode is activated at the switch by the surgeon and/or to call for the Coagulation Waveform to be created at the ESG and channeled through the conductive means to one or more Coagulation Electrodes, such as Energy Window Electrodes.

In addition, given the heat that can be generated around electrosurgical electrodes, in some instances is of value to monitor the temperature of the electrode and/or provide a mechanism to prevent the temperature from exceeding a pre-determined limit.

As used herein, the term "coagulation" should be construed to encompass effects other than strictly coagulative effects, including, for example, any therapeutic effect from heating, including denaturing collagen & elastin, melting fat, disabling nerves and sweat glands. Thus, Coagulation Electrodes, such as Energy Window Electrodes, may be configured to deliver energy designed to perform any of these tissue-altering functions.

In one embodiment, the TDM may comprise two active electrodes and may be configured to allow a user to select from device modes via a means for switching between a plurality of electrosurgical energy modes (a "Switching Means"), which may be positioned in the TDM handle. In some embodiments, the Switching Means may be configured to allow for selection between 3 settings (neutral, CUT mode, and COAG mode). In some such embodiments, the Switching Means may be further configured to provide for 5 possible position configurations within such settings, i.e., Neutral (1 position configuration), CUT Mode (2 position configurations), and COAG Mode (2 position configurations). In some embodiments, it may be important that RF energy not be continuously connected to any circuit when in neutral setting. In the neutral setting, (no button switches pressed), it is preferred that Circuit 1/RF Source Circuit is open and therefore not electrically coupled to any electrode. Likewise, the signal circuits are preferably open in this setting. However, as discussed below, some embodiments are contemplated in which an electrical path to the patient and/or electrode(s) is closed in the neutral mode but a signal circuit to an ESG is open in this mode.

In selecting one electrode in a particular Mode, in some embodiments, the Switching Means may be configured to decrease the possibility that the unselected electrode(s) is energized while selecting the selected electrode(s). In some such embodiments, the Switching Means may be configured to physically decouple the unselected electrode(s) during the process of selecting the other electrode(s). In other embodiments, the Switching Means may be configured to move the unselected electrode away from the Circuit 1/RF Source during the process of selecting the other electrode(s) to reduce the chances of arcing or other similar problems but may not actually physically decouple the unselected electrode (because it may be already physically separated from the RF source in the neutral setting). In some embodiments, the Switching Means may first decouple the signal circuit and then decouple the Circuit 1/RF Source connection to the unselected electrode before closing the selected electrode circuits. The activation of the switch may then first close the electrical connection for the Circuit 1/RF Source to the desired electrode(s) Cutting Electrode(s) or Coagulation Electrode(s) and subsequently close the Circuit 2/CUT Mode Signal or Circuit 3/COAG Mode Signal circuit. In preferred embodiments, this sequence of closing circuits and/or opening or decreasing the possibility of undesired closing of other circuits may be performed automatically due to the structure of the switching assembly.

In some embodiments, the switch assembly or switching means may further be configured to automatically accomplish a desired sequence of deactivation when a particular mode is deselected, such as, for example, when a user lifts his or her finger from a button or switch of a TDM or other electrosurgical device. For example, some embodiments that are configured to make an electrical connection to the patient/electrode first and then subsequently close the path to the ESG to tell it which mode to activate may further be configured to decouple the various electrical paths in a precise sequence opposite to the activation sequence, namely, the ESG path may be opened first during de-activation, after which the path to the patient/electrode may be opened By providing switch assembly or switching means that ensures that the activation, and deactivation, of the electrical paths to the patient and ESG take place sequentially, rather than simultaneously, and in the proper order, arcing/sparking and other such problems may be avoided.

FIG. 1A illustrates a preferred embodiment of an electrosurgical system 100 comprising a switching assembly 150, as described above. In the depicted embodiment, system 100 comprises a TDM system 100 that comprises an ESG 180 and a TDM device 120. ESG 180 comprises a 3-pinned plug receptacle 181 that comprises pin receptacles 181A, 181B, and 181C. Pin receptacle 181A is for Circuit 1/RF Source Circuit. Pin receptacles 181B&C are signal circuits for the CUT & COAG Modes, respectively.

TDM device 120 further comprises tip 130, handle 122, source/signal wire 123, and 3-pinned plug 124. The 3-pinned plug 124 comprises pins 124A, 124B, and 124C: Pin 124A is part of the Circuit 1/RF Source Circuit while pins 124B&C are parts of the Circuit 2/CUT Mode Signal Circuit and Circuit 3/COAG Mode Signal Circuit, respectively. The 3-pinned plug 124 may connect into ESG receptacle 181 having corresponding pin receptacles 181A, 181B, and 181C. Handle 122 may receive source/signal wire 123 and house the switching assembly 150, which is one example of a switching means, as described above.

Figure 1B:
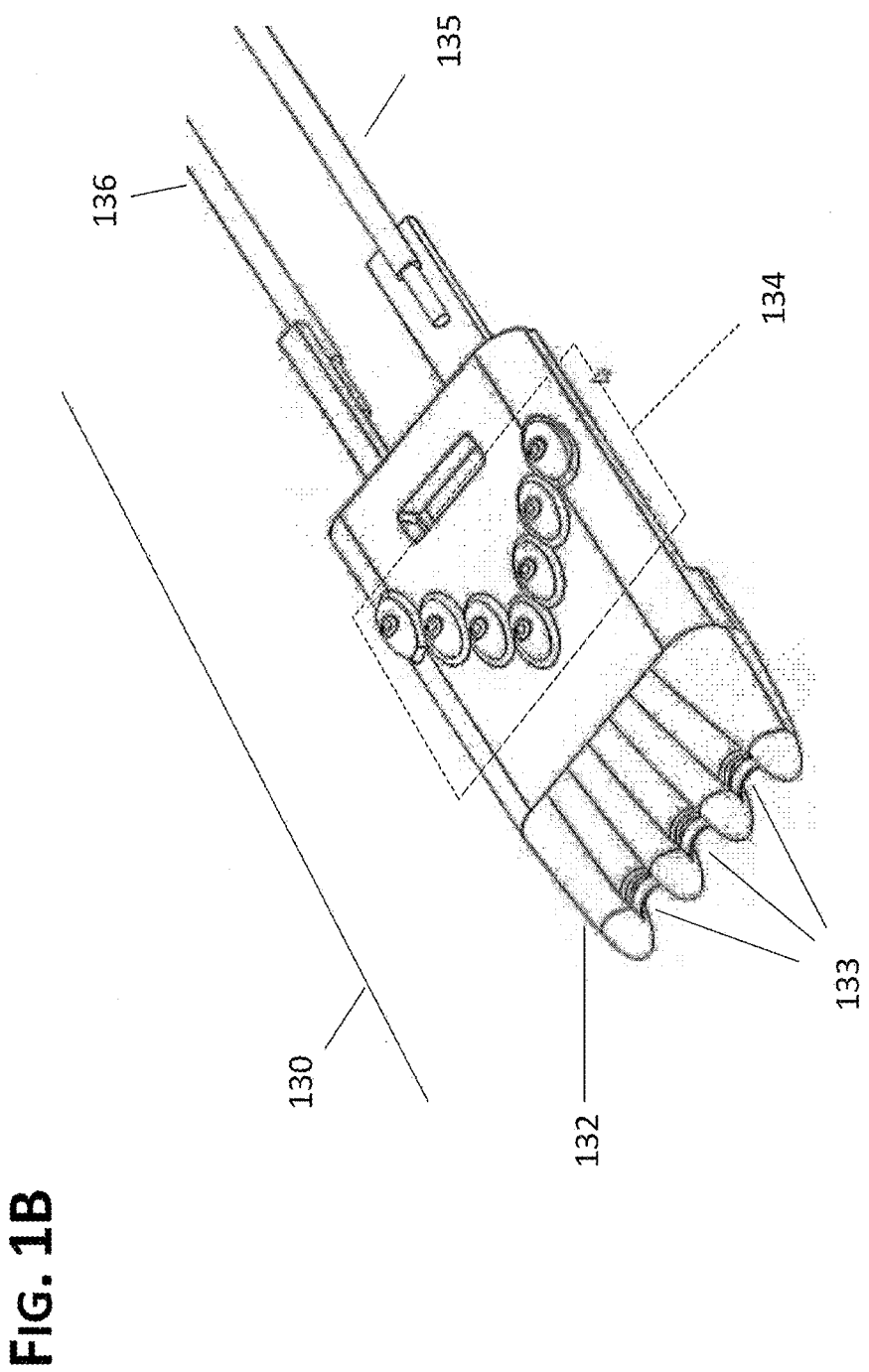
FIG. 1B is a close-up, perspective view of a Tissue Dissector and Modifier tip and its components.

FIG. 1B illustrates tip 130 that may comprise a housing 132, which may be made up of a ceramic or other preferably non-conductive material. Cutting Electrode 133 may comprise a plurality of segments. Such segments may be positioned in between a plurality of protrusions 131 positioned at the distal end of tip 130. Tip 130 further comprises a plurality of Coagulation electrodes 134 positioned within an Energy Window. Electrodes 134 terminate at 7 termini atop 7 apices in a chevron configuration. Cutting electrode wire lead 135 and energy window electrode wire lead 136 extend from a proximal end of tip 130. Housing 132 may comprise one or more bulbous protrusions 131 between which are located the recessed segments of Cutting Electrode 133 that distribute Cut/Blend RF waveforms.

In order to prevent arcing, sparking, or other unwanted electrical events, the Cutting Electrode(s) and Coagulation Electrode(s) are preferably separated dielectrically when coming in close proximity using dielectric materials, for example, Kapton® material and/or high temperature epoxies.

FIGS. 2A and 2B illustrate an embodiment of a switching assembly 250 comprising one example of a switching means for switching between cutting and coagulation RF waveforms. Switching assembly 250 comprises rocker 251, contact spring 252, and switchboard 260. Switchboard 260 comprises RF Source Circuit trace 261A, CUT Mode signal trace 261B, and COAG Mode Signal trace 261C. Switchboard 260 further comprises Cut or Blend RF output trace 265 and Coag/Energy Window RF output trace 266. Switchboard 260 further comprises two dome switches 262 and 263, each of which is configured to close a signal circuit (CUT and COAG, respectively) when depressed by one of the two plungers 251B (CUT) or 251C (COAG) of rocker 251. Contact spring 252 may be coupled to switchboard 260 atop RF Source Circuit input trace 261A and thus carries the RF energy to the appropriate electrode path.

Because of the characteristics of high voltage RF energy, it is not a preferred method to activate each specific mode in one step. Otherwise, potentially dangerous arcing and sparking may occur. For patient and user safety, as well as the durability of the TDM device or other electrosurgical device, it is preferred to employ two steps for each mode activation: (1) to complete the path from the RF source line to the chosen electrode and then (2) to signal the ESG to activate and deliver the chosen RF energy to the patient via the path defined by the RF source lead, the switch assembly 250 and its traces, the specific wire leading to the desired cut or coag electrode(s), and the electrode. In some embodiments, at least 3 mm of clearances may be provided between all traces and current carrying components. Thus, in some embodiments, at least a 3 mm clearance may be provided between an output trace associated with an unselected electrode before contact is made with an output trace of a selected electrode. In some embodiments, this clearance may be provided in a neutral setting. Alternatively, this clearance may only be provided upon activation of a selected electrode during operation of the switching assembly 250. Thus, in some embodiments, a clearance, but an insufficient clearance, may be provided in a neutral setting and this clearance distance may be increased during actuation of switching assembly 250. Alternatively, no clearance may be provided in a neutral setting and sufficient clearance may be provided during actuation of switching assembly 250, as described in greater detail below.

Figure 2C:
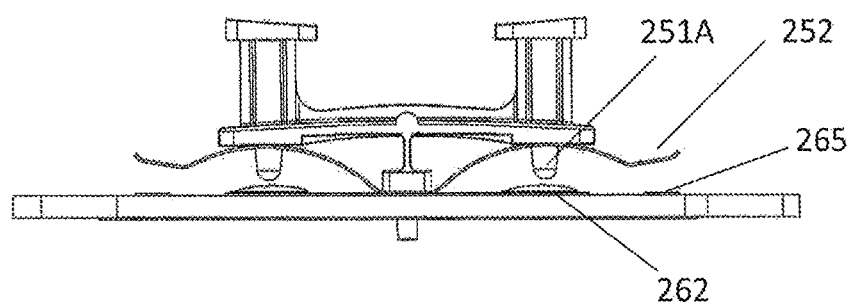
FIG. 2C is a side elevation view of a switch assembly in the neutral setting.

Switch assembly 250 may be configured to operate using 5 settings, one of which may be a default or neutral setting not requiring any user interaction, two of which may be sequentially selected during operation of switch assembly 250 in one direction and/or with respect to one primary mode of operation (CUT or COAG), and the other two of which may be sequentially selected during operation of switch assembly 250 in the other direction and/or with respect to the other primary mode of operation. More particularly, switch assembly 250 may be configured to operate in the following settings/positions:

1) Neutral in which no signal circuit is closed (no plunger (251B or C is depressing a dome switch 262 or 263)). In some cases (including the embodiment depicted in FIG. 2A), neutral may further mean that no RF path to an electrode is made (by each foot of the contact spring having sufficient clearance from RF output path traces 265 and 266 beneath them). FIG. 2C further illustrates the neutral position in that plunger 251A is not depressing dome switch 262 and contact spring 252 is not making contact with Cut/Blend RF output trace 265.

Figure 2D:
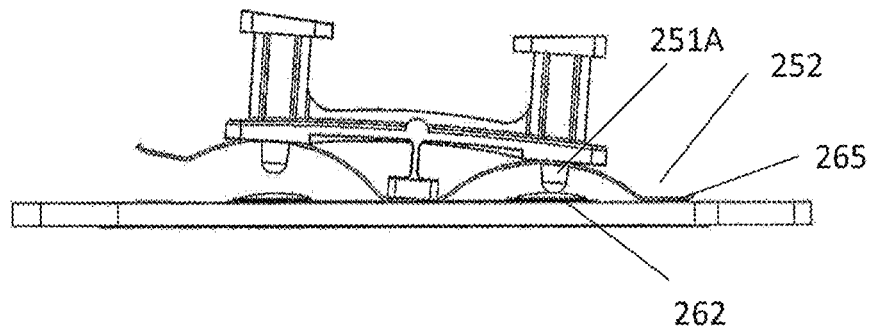
FIG. 2D is a side elevation view of a switch assembly in the CUT setting #1.

2) CUT Setting 1 in which the RF path to the Cutting Electrode is made (contact spring 252 contacts Cut/Blend RF output trace 265) but Circuit 2/CUT Mode Signal Circuit is not yet closed (dome switch 262 has not yet been depressed by plunger 251B). FIG. 2D further illustrates the CUT Setting 1 position in that plunger 251A is not depressing dome switch 262 but contact spring 252 is making contact with Cut/Blend RF output trace 265. The depicted embodiment is configured to automatically transition to CUT Setting 1 upon depressing the button of rocker 251 corresponding with (atop) plunger 251A and, as discussed below, to transition automatically to CUT setting 2 upon further depression of this button.

Figure 2E:
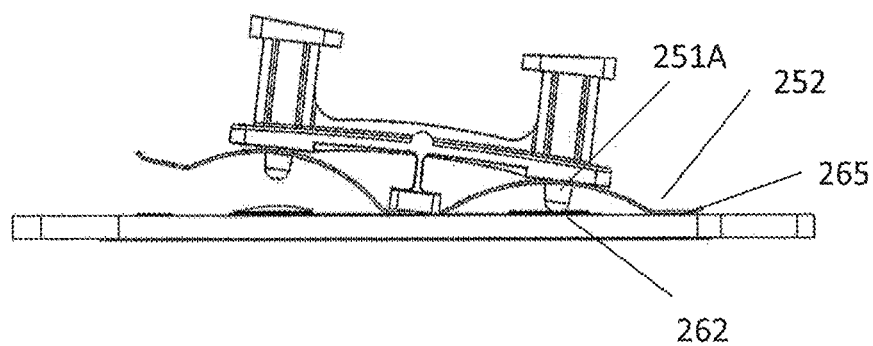
FIG. 2E is a side elevation view of a switch assembly in the CUT setting #2.

3) CUT Setting 2 in which the RF path to the Cutting Electrode remains made and Circuit 2/CUT Mode Signal Circuit is closed by depressing dome switch 262 with plunger 251A, thereby causing the ESG to generate and send Cut or Blend RF energy through the RF Cut Circuit to the Cutting Electrode. FIG. 2E illustrates the CUT Setting 2 position in that plunger 251A is depressing dome switch 262 after contact spring 252 has made contact with Cut/Blend RF output trace 265. As mentioned above, the depicted embodiment, and other embodiments depicted herein, is configured to allow for making this important transition of electrical contacts simply by pressing on one side of rocker 251.

4) COAG Setting 1 in which the RF path to the Coagulation Electrode (in this case, the Energy Window Electrode) is made but Circuit 3/COAG Mode Signal Circuit is not yet closed. This position is not illustrated but is the mirror image of FIG. 2D on the left side of the switch assembly 250 from the perspective of the figure.

5) COAG Setting 2 in which the RF path to the Energy Window Electrode remains made and Circuit 3/COAG Mode Signal Circuit is closed, thereby causing the ESG to generate Coagulation RF Waveforms that flow through the RF COAG circuit to the Energy Window Electrode. This position is not illustrated but is the mirror of FIG. 2E on the left side of the switch assembly 250 from the perspective of the figure.

Some embodiments may further be configured such that the switch assembly 250 is configured to perform the precise sequence described above in reverse when a particular electrode activation mode is being disabled or turned off. For example, when a user removes a force on one side of switch assembly 250 (say, the CUT side), the Circuit 2/CUT Mode Signal Circuit may first be opened by releasing plunger 251A from dome switch 262. Switch assembly 250 may be configured to subsequently open the RF path to the Cutting Electrode(s) and/or patient by lifting contact spring 252 from Cut/Blend RF output trace 265. The same may be true with respect to the opposite side/mode. As mentioned elsewhere herein, switch assembly 250 (or any of the other switch assemblies or switching means disclosed herein) may be configured to allow for this precise, sequential activation, and deactivation, of these electrical paths/circuits automatically simply by depressing a button, switch, or the like and, similarly, releasing the button, switch, or the like.

Notwithstanding the foregoing, it is contemplated that, for use in connection with certain electrosurgical devices and/or for certain applications, it may be acceptable to provide a switch assembly or switching means that is configured to operate in essentially three modes rather than five. More particularly, in some embodiments, any of the switch assemblies disclosed herein may be modified such that depressing a particular button, switch, or portion of a button/switch/etc. associated with a particular mode may result in simultaneous, or at least substantially simultaneous, closing of both the path to the patient and/or electrode(s) and the signal path to the ESG for both of the respective modes/electrodes. Preferably, a neutral mode is still provided between the other two modes.

FIGS. 3A and 3B illustrate another embodiment of a switch assembly 350 that may be used in a TDM system or another electrosurgical device or system. Switch assembly 350 is another example of a means for switching between a plurality of electrosurgical energy modes. Switch assembly 350 comprises rocker 351, CUT Contact Spring 352B, Coag contact spring 352C, and switchboard 360.

Switchboard 360 comprises RF Source trace 361A, CUT Mode Signal trace 361B, and COAG Mode Signal trace 361C. Switchboard 360 further comprises Cut or Blend RF output trace 365 and Coag/Energy Window RF output trace 366. Switchboard 360 further comprises two dome switches 362 and 363, each of which is configured to close a signal circuit (CUT or BLEND and COAG, respectively) when depressed by one of the two plungers 351B (CUT or BLEND) or 351C (COAG) of rocker 351. CUT contact spring 352B is configured to complete a path between the RF Source trace 361A and Cut/blend RF output trace 365. COAG contact spring 352C is configured to complete a path between the RF Source trace 361A and COAG RF output trace 366.

FIG. 3C illustrates how CUT contact spring 352B may comprise one piece at least substantially in the shape of a "U" when viewed from a top plan view perspective. This U shape, however, may curve from an elevation view perspective to allow for contacting one or more RF source traces into the rocker structure 351. A similar U-shaped shape or other similar shape may be provided on the opposite side if desired for the other electrosurgical mode traces.

Figure 3D:
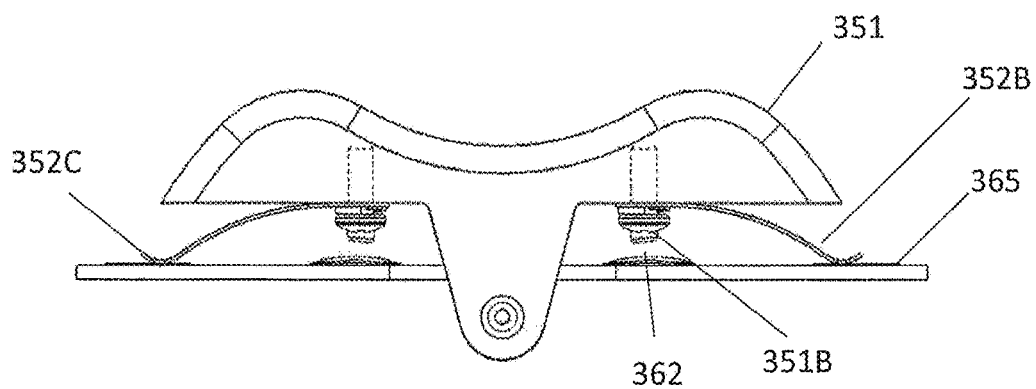
FIG. 3D is a side elevation view of a switch assembly in the neutral setting.

Switch assembly 350 may be configured to operate using 5 settings, one of which may be a default or neutral setting not requiring any user interaction, two of which may be sequentially selected during operation of switch assembly 350 in one direction and/or with respect to one primary mode of operation (CUT or COAG), and the other two of which may be sequentially selected during operation of switch assembly 350 in the other direction and/or with respect to the other primary mode of operation. Unlike switch assembly 250, however, switch assembly 350 is configured such that, in the neutral setting, the opposing contact springs 352B and 352C are configured to be in contact with their respective RF source traces. More particularly, switch assembly 350 may be configured to operate in the following settings/positions:

1) Neutral, in which no signal circuit is closed (no plunger (351BorC is depressing a dome switch 362 or 363)). In this embodiment, however, contact springs 352B and 352C are permitted to contact the RF source and RF carry-away traces in the neutral setting because the contact between contact springs 352B and 352C and their respective traces in this configuration serve to center and position the rocker mechanism flat when the user is not depressing either end of the rocker. FIG. 3D further illustrates the neutral setting in that plunger 351B is not depressing dome switch 362 (nor is the opposite plunger depressing its respective dome switch).

Figure 3E:
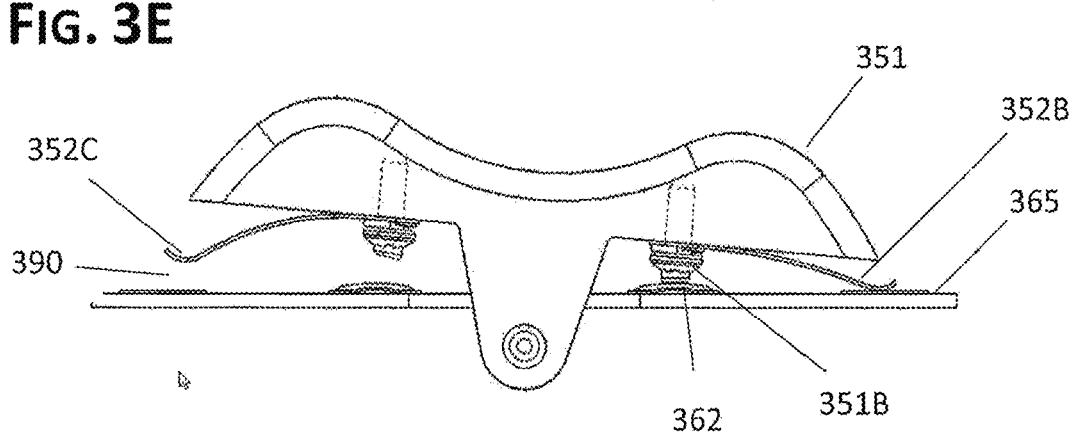
FIG. 3E is a side elevation view of a switch assembly in the CUT setting #1.

2) FIG. 3E illustrates CUT Setting 1 in which (A) the RF path to the Cutting Electrode continues to be made (contact spring 352B contacts RF source trace 361A (visible) and Cut/Blend RF output trace 365 (not visible, hidden from view)), (B) however, COAG contact spring 352C breaks any contact with RF source trace 361A and COAG/Energy Window RF output trace 366, as depicted in FIG. 3D, thereby creating a clearance that is preferably sufficient to avoid arcing between the conductive components, and (C) the Circuit 2/CUT Mode Signal Circuit is not yet closed (dome switch 362 has not yet been depressed by plunger 351B). FIG. 3E further illustrates the CUT Setting 1 position in that plunger 351B is not depressing dome switch 362 and clearance 390 is visible as 352C lifts away from the traces beneath it.

Figure 3F:
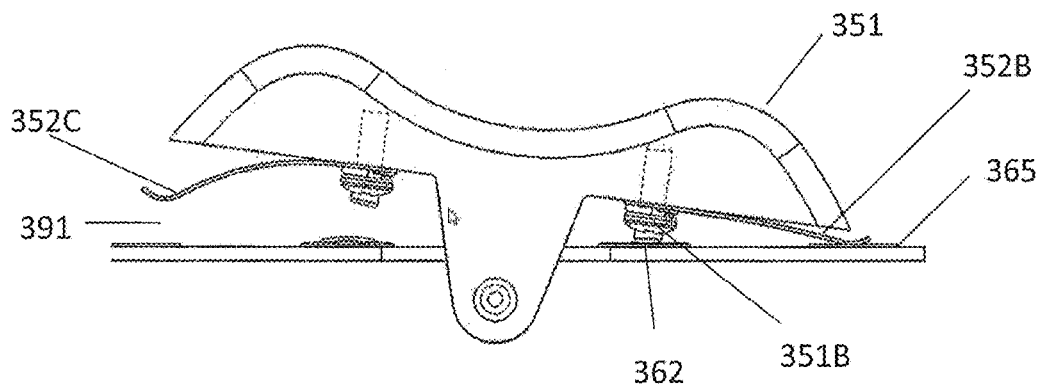
FIG. 3F is a side elevation view of a switch assembly in the CUT setting #2.

3) FIG. 3F illustrates CUT Setting 2 in which (A) the RF path to the Cutting Electrode remains closed, (B) the CUT Mode Signal Circuit is also closed, thereby causing the ESG to send Cut or Blend RF Waveforms through the RF CUT circuit to the Cutting Electrode, and (C) COAG Contact Spring 352C reaches a minimum clearance preferably sufficient to avoid arcing, sparking, or other undesired electrical events. In some embodiments, this clearance may be at least 3 mm. FIG. 3F illustrates the CUT Setting 2 position in which plunger 351B has depressed dome switch 362 and contact spring 352B continues making contact between RF Source trace 361A and the Cut/Blend RF output trace 365. Maximum clearance, as shown at 391, is achieved in this figure, which may be 3 mm or more. In the embodiment of assembly 350, the device may be configured such that the sequence depicted in FIGS. 3D-3F, along with a related sequence in an opposite direction (not shown in the drawings) may take place automatically upon depressing one side (or the other) of the top of rocker 351.

4) COAG Setting 1 in which (A) the RF path to the Coagulation/Energy Window Electrode(s) remains closed, (B) the RF path to the Cutting Electrode is open, but (C) Circuit 3/COAG Mode Signal Circuit is not yet closed. This position is not illustrated but is the mirror image of FIG. 3E on the opposite end of the switch assembly.

5) COAG Setting 2 in which (A) the RF path to the Coagulation/Energy Window Electrode(s) remains closed, (B) the RF path to the Cutting Electrode remains open, but (C) Circuit 3/COAG Mode Signal Circuit is now closed, thereby causing the ESG to send Coagulation RF Waveforms through the RF COAG circuit to the Coagulation/Energy Window Electrode(s). This position is not illustrated but is the mirror image of FIG. 3F but on the opposite end of the switch assembly.

Some embodiments may further be configured such that the switch assembly 350 is configured to perform the precise sequence described above in reverse when a particular electrode activation mode is being disabled or turned off. For example, when a user removes a force on one side of switch assembly 350 (say, the CUT side), the Circuit 2/CUT Mode Signal Circuit may first be opened by releasing dome switch 362 from plunger 351B. Switch assembly 350 may be configured to subsequently close the RF path to the COAG Electrode(s) and/or patient on the opposite side. The RF path to the selected electrode(s) (CUT in the scenario described above) remains closed during the entire operation between the neutral and CUT mode. As mentioned elsewhere herein, switch assembly 350 (or any of the other switch assemblies or switching means disclosed herein) may be configured to allow for this precise, sequential activation, and deactivation, of these electrical paths/circuits automatically simply by depressing a button, switch, or the like and, similarly, releasing the button, switch, or the like.

Figure 4A:
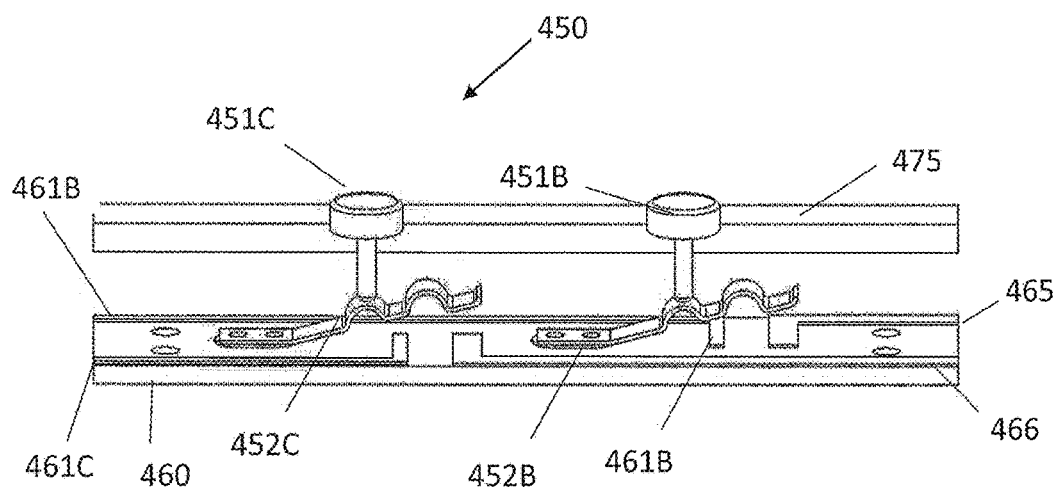
FIG. 4A is a side perspective view of another embodiment of a switch assembly in the neutral setting.
Figure 4B:
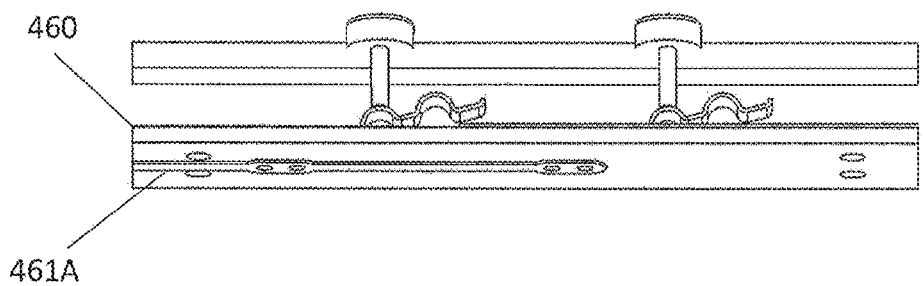
FIG. 4B is a lower perspective view of the switch assembly of FIG. 4A.

FIGS. 4A and 4B illustrate another embodiment of a switch assembly 450. Switch assembly 450 is also another example of a switching means for switching between cutting and coagulation RF waveforms that may be used in a TDM or another electrosurgical system. Switch assembly 450 comprises outer housing 475, CUT contact spring 452B, COAG contact spring 452C, CUT plunger 451B, COAG plunger 451C, and switchboard 460.

Switchboard 460 comprises RF Source trace 461A, CUT Signal trace 461B, and COAG Signal trace 461C. Switchboard 460 further comprises Cut/blend RF output trace 465 and Coagulation/Energy Window RF output trace 466. CUT contact spring 452B is affixed atop RF Source trace 461A and thus will carry the Cut/Blend RF Waveform current to Cutting Electrode path when the ESG is so activated. Similarly, COAG contact spring 452C is also affixed atop RF Source trace 461A and thus will carry the Coagulation RF Waveform to the Coagulation/Energy Window Electrode path when the ESG is so activated.

Switch assembly 450 may be configured to operate in the following settings/positions:

1) Neutral in which no signal circuit is closed (no plunger (451B or 451C) is pressing down on either spring 452B or 452C), thus no RF path to an electrode is closed by any pad of either CUT contact spring 452B or COAG contact spring 452C, and preferably each contact spring has sufficient clearance from RF output path traces 465 and 466 beneath them to avoid arcing, sparking, etc.

Figure 4C:
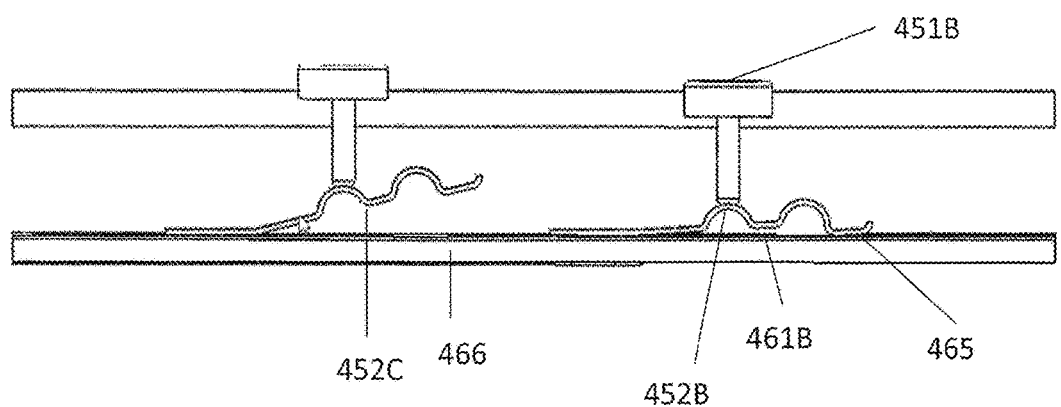
FIG. 4C is a side elevation view of a switch assembly in the CUT setting #1.

2) FIG. 4C illustrates CUT Setting 1 in which (A) the RF path to the Cutting Electrode is closed (plunger 451B sufficiently depresses contact spring 452B so that it contacts Cut/Blend RF output trace 465) but (B) the Circuit 2/CUT Mode Signal Circuit is not yet closed because CUT contact spring 452B is not yet contacting CUT Mode signal trace 461B, and (C) COAG contact spring 452C continues to have sufficient clearance away from the Coagulation/Energy Window RF trace 466 to avoid acing, sparking, etc. In some embodiments, one or both of contact springs 452B and 452C may be bent or otherwise shaped to facilitate closing the RF path(s) before the respective signal circuit paths. Alternatively, or additionally, the respective signal contacts may be shaped and/or positioned to facilitate the desired staging of these electrical connections.

Figure 4D:
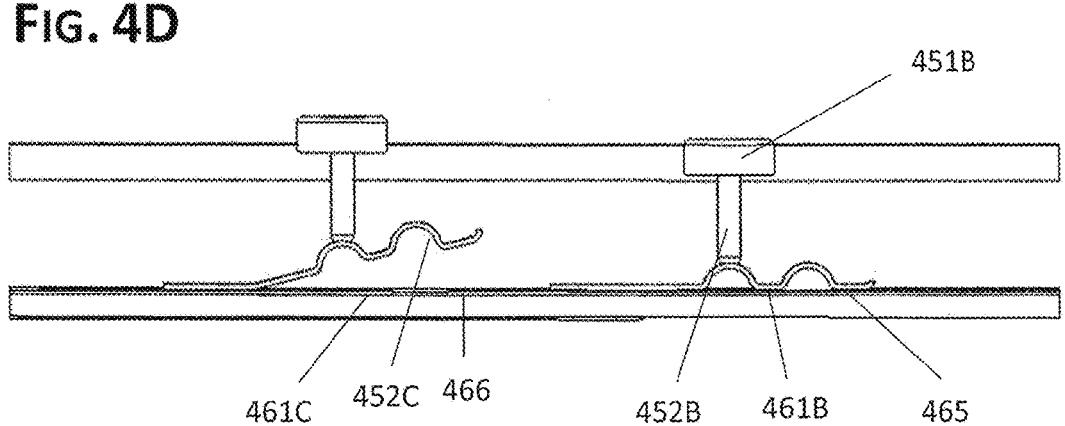
FIG. 4D is a side elevation view of a switch assembly in the CUT setting #2.

3) FIG. 4D illustrates CUT Position 2 in which (A) the RF path to the Cutting Electrode remains closed, as mentioned in the previous paragraph, but in which (B) CUT contact spring 452B makes contact with CUT signal trace 461B, which completes the circuit to the ESG causing the ESG to deliver a Cut/Blend RF Waveform to the RF source line and eventually to the Cutting Electrode via CUT contact spring 452B. Preferably, COAG contact spring 452C continues to have sufficient clearance away from the Energy Window RF output trace 466 to eliminate arcing and/or sparking, etc.

4) COAG Position 1 in which (A) the RF path to the Coagulation/Energy Window Electrode(s) is closed but (B) Circuit 3/COAG Mode Signal Circuit is not yet closed. This position is not illustrated in the drawings. However, the positions of springs 452C and 452B in FIG. 4C would be reversed.

5) COAG Position 2 in which (A) the RF path to the Coagulation/Energy Window Electrode(s) remains closed and (B) the pad on COAG contact spring 452C has been moved downward sufficiently to contact the COAG Mode signal trace 461C thus causing Circuit 3/COAG Mode Signal Circuit to close and causing the ESG to send Coagulation RF Waveforms through the RF COAG circuit to the Coagulation/Energy Window Electrode(s) via COAG contact spring 452C. This position is not illustrated but is the mirror image of FIG. 4D but on the left side of the switch assembly. In other words, the positions of springs 452B and 452C in FIG. 4D would be reversed for COAG position 2.

In alternative embodiments, each spring/plunger/trace combination may be positioned on a separate switchboard.

Some embodiments may further be configured such that the switch assembly 450 is configured to perform the precise sequence described above in reverse when a particular electrode activation mode is being disabled or turned off. For example, when a user removes a force on one of the buttons/plungers of switch assembly 450 (say, plunger 451B), the Circuit 2/CUT Mode Signal Circuit may first be opened by releasing CUT contact spring 452B from CUT signal trace 461B. Switch assembly 450 may be configured to subsequently open the RF path to the Cutting Electrode(s) and/or patient by lifting contact spring 452B from Cut/Blend RF output trace 465. The same may be true with respect to the opposite side/mode. This effect may be provided for by designing suitable bends into the two contact springs. As mentioned elsewhere herein, switch assembly 450 (or any of the other switch assemblies or switching means disclosed herein) may be configured to allow for this precise, sequential activation, and deactivation, of these electrical paths/circuits automatically simply by depressing a button, switch, or the like and, similarly, releasing the button, switch, or the like. In this particular embodiment, both of the two plungers buttons are separately configured to provide for a desired sequential activation and deactivation of the electrical paths/circuits.

Figure 5A:
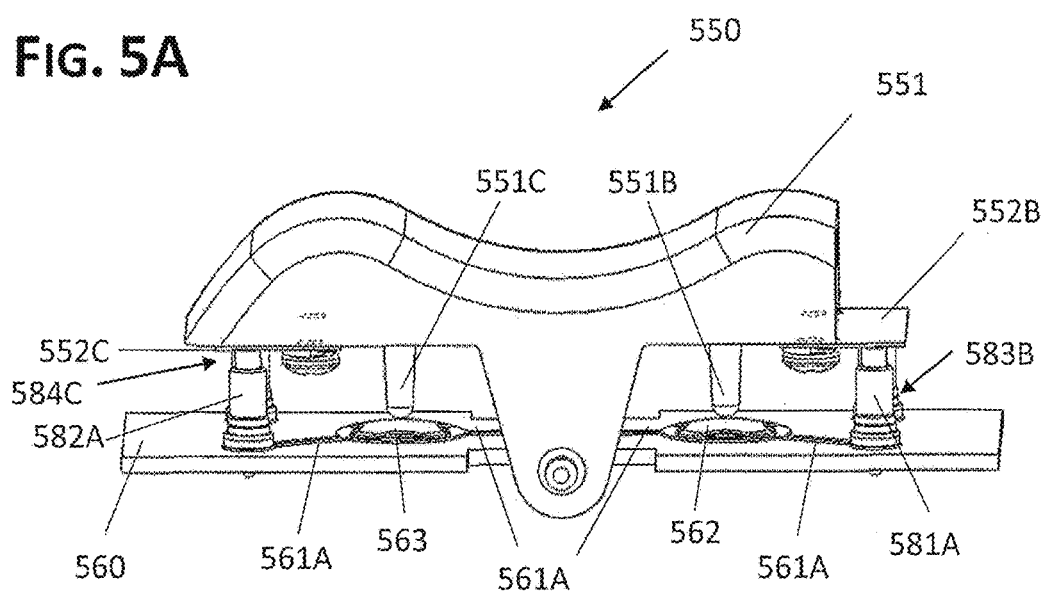
FIG. 5A is a side perspective view of yet another embodiment of a switch assembly illustrate with part of the rocker cut away to reveal a contact bridge of the switch assembly.

FIG. 5A illustrates another embodiment of a switch assembly 550 that may be used in a TDM system or another electrosurgical device or system. Switch assembly 550 is another example of a means for means for switching between a plurality of electrosurgical energy modes. Switch assembly 550 comprises rocker 551, CUT Contact Bridge 552B, Coag contact Bridge 552C, switchboard 560, and 4 pogo-pins 581A, 582A, 583B (behind 581A), and 584C (behind 582A). Each pogo-pin may comprise two or more nested cylinders with an internal spring mechanism that returns the pin back to a pre-determined length after compression. Pogo-pins may be conductive and may be capable of making circuits with RF waveforms. Pogo-pins 581A and 582A are the RF Source pins to make separate paths to the Cutting Electrode(s) and the Coagulation/Energy Window Electrode(s) for the CUT Mode and the COAG Mode, respectively. Pogo-pin 583B electrically connects to the electrical pathway of the Cutting Electrode(s). Pogo-pin 584C electrically connects to the electrical pathway of the Coag/Energy Window Electrode(s).

Figure 5B:
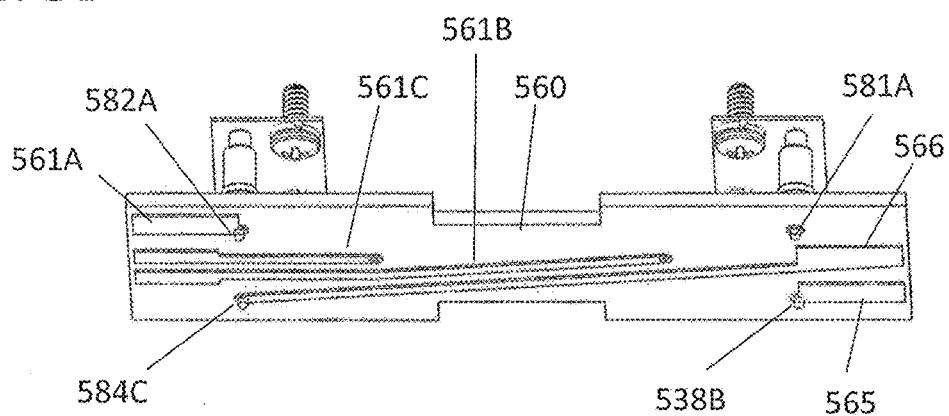
FIG. 5B is a lower perspective view of the switch assembly of FIG. 5A.

In FIGS. 5A and 5B, switchboard 560 comprises RF Source trace 561A (connecting both RF Source pogo-pins 581A and 582A and dome switches 562 and 563), CUT Mode Signal trace 561B, and COAG Mode Signal trace 561C. Switchboard 560 further comprises Cut or Blend RF output trace 565 and Coag/Energy Window RF output trace 566. Switchboard 560 further comprises two dome switches 562 and 563, each of which is configured to close a signal circuit (CUT or BLEND and COAG, respectively) when depressed by one of the two plungers 551B (CUT or BLEND) or 551C (COAG) of rocker 551. CUT Contact Bridge 552B is configured to electrically connect, upon depression of the CUT Mode side of the rocker, RF Source trace 561A and Cut/Blend RF output trace 565 via RF Source CUT Pogo-pin 581A and Cut or Blend RF output Pogo-pin 583B. COAG Contact Bridge 552C is configured to electrically connect, upon depression of the other side of the rocker (the COAG Mode rocker side), RF Source trace 561A and Coag/Energy Window RF output trace 566 via RF Source COAG Pogo-pin 582A and COAG RF output Pogo-Pin 552C.

FIG. 5A illustrates how CUT Contact Bridge 552B may comprise one piece of conductive material substantially in the shape of a rectangle when viewed from a top plan view perspective. This rectangular shape may permit it to be affixed to the rocker on one side while serving as a conductive bridge between the two pogo-pins on the CUT Mode circuit 581A and 583B.

A similar rectangular-shaped shape or other similar or suitable shape may be provided on the opposite side if desired for the other electrosurgical mode traces.

Figure 5C:
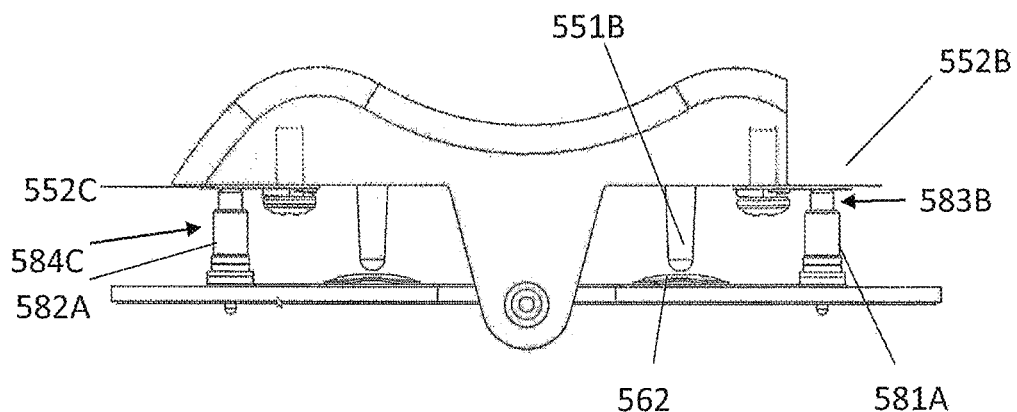
FIG. 5C is a side elevation view of the switch assembly in a neutral setting.
Figure 5D:
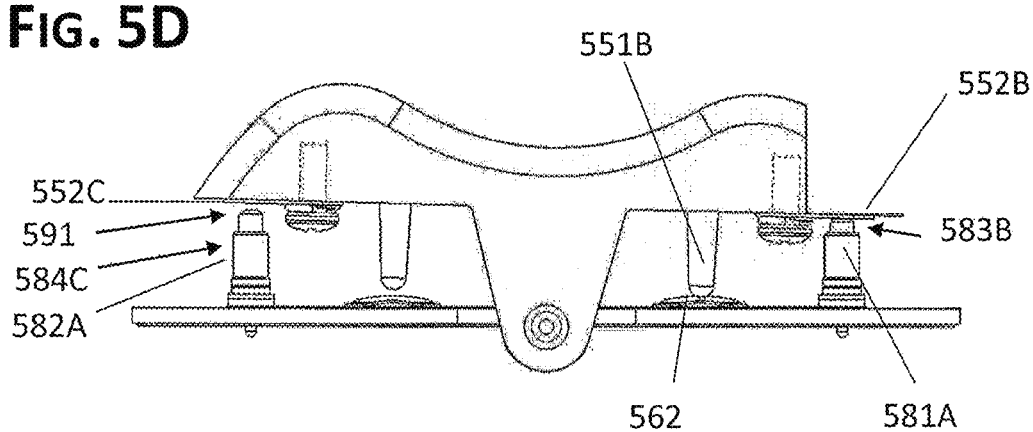
FIG. 5D is a side elevation view of the switch assembly in a first CUT setting.
Figure 5E:
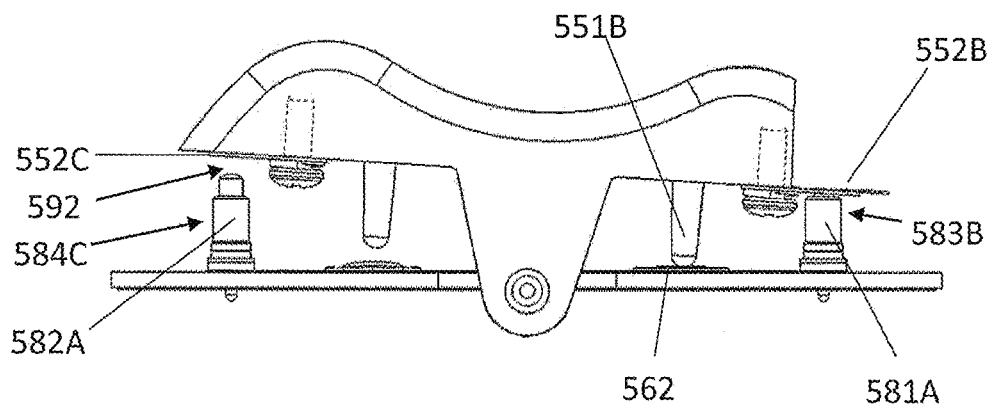
FIG. 5E is a side elevation view of the switch assembly in a second CUT setting.

Switch assembly 550 may be configured to operate using 5 settings, one of which may be a default or neutral setting not requiring any user interaction, two of which may be automatically, sequentially selected during operation of switch assembly 550 in one direction and/or with respect to one primary mode of operation (CUT or COAG), and the other two of which may be automatically, sequentially selected during operation of switch assembly 550 in the other direction and/or with respect to the other primary mode of operation. Unlike switch assembly 250, however, switch assembly 550 is configured such that, in the neutral setting, the opposing contact bridges 552B and 552C are configured to be in contact with their respective RF source traces and signal traces via the respective pogo-pins. More particularly, switch assembly 550 may be configured to operate in the following settings/positions:

1) Neutral, in which no signal circuit is closed (no plunger (551BorC is depressing a dome switch 562 or 563)). In this embodiment, however, contact bridges 552B and 552C are permitted to contact the RF source pogo-pins 581A and 582A and RF carry-away pogo-pins 583B and 584C in the neutral setting because the contact between contact bridges 552B and 552C and their respective pogo-pins in this configuration serves to center and position the rocker mechanism flat when the user is not depressing either end of the rocker. FIG. 5C illustrates the neutral setting in that plunger 551B is not depressing dome switch 562 (nor is the opposite plunger depressing its respective dome switch).
2) CUT Setting 1 in which (A) the RF path to the Cutting Electrode(s) continues to be made (contact bridge 552B contacts RF source pogo-pin 581A and Cut/Blend RF output pogo-pin 583B), (B) however, COAG contact bridge 552C breaks any contact with RF source pogo-pin 582A and COAG/Energy Window RF output pogo-pin 584C, as depicted in FIG. 5D, thereby creating a clearance 591 that is preferably sufficient to avoid arcing between the metal components (at least 3 mm in some embodiments), and (C) the Circuit 2/CUT Mode Signal Circuit is not yet closed (dome switch 562 has not yet been depressed by plunger 551B). FIG. 5D illustrates the CUT Setting 1 position in that plunger 551B is not depressing dome switch 562 and clearance 591 is visible as contact bridge 552C lifts away from the pogo-pins beneath it.
3) CUT Setting 2 in which (A) the RF path to the Cutting Electrode(s) remains closed by the bridge as disclosed in the previous step, (B) the CUT Mode Signal Circuit is also closed by depression of dome switch 562, thereby causing the ESG to send Cut or Blend RF Waveforms through the RF CUT circuit through pogo-pin 581A through contact bridge 583B through Cut or Blend RF output trace 583B to Cut or Blend RF output trace 565 to the Cutting Electrode(s), and (C) COAG Contact bridge 552C reaches a minimum clearance 592, preferably sufficient to avoid arcing, sparking, or other undesired electrical events. In some embodiments, this clearance may be at least 3 mm. FIG. 5E illustrates the CUT Setting 2 position in which plunger 551B has depressed dome switch 562 and contact bridge 552B continues making contact between Cut or Blend RF Source pogo-pin 581A and the Cut/Blend RF output pogo-pin 583B. Maximum clearance, as shown at 592, is achieved in this figure, which may be 3 mm or more. In the embodiment of assembly 550, the device may be configured such that the sequence depicted in FIGS. 5C-5E, along with a related sequence in an opposite direction (not shown in the drawings) may take place automatically upon depressing one side (or the other) of the top of rocker 551.
4) COAG Setting 1 in which (A) the RF path to the Coagulation/Energy Window Electrode(s) remains closed, (B) the RF path to the Cutting Electrode is now open, but (C) Circuit 3/COAG Mode Signal Circuit is not yet closed. This position is not illustrated but is the mirror image of FIG. 5D on the opposite end of the switch assembly.
5) COAG Setting 2 in which (A) the RF path to the Coagulation/Energy Window Electrode(s) remains closed, (B) the RF path to the Cutting Electrode remains open, but (C) Circuit 3/COAG Mode Signal Circuit is now closed, thereby causing the ESG to send Coagulation RF Waveforms through the RF COAG circuit to the Coagulation/Energy Window Electrode(s). This position is not illustrated but is the mirror image of FIG. 5E but on the opposite end of the switch assembly.

In some embodiments, the switch assembly 550 may be configured to perform the precise sequence described above in reverse when a particular electrode activation mode is being disabled or turned off. For example, when a user removes a force on one side of the rocker of switch assembly 550 (say, the CUT side) after activating and using the CUT mode, the Circuit 2/CUT Mode Signal Circuit may first be opened by releasing plunger 551B from dome switch 562. Switch assembly 550 may be configured to subsequently decrease and, ultimately, eliminate clearance 591 and allow COAG contact bridge 552C to make contact with RF source pogo-pin 582A and COAG/Energy Window RF output pogo-pin 584C. As mentioned elsewhere herein, switch assembly 550 (or any of the other switch assemblies or switching means disclosed herein) may be configured to allow for this precise, sequential activation, and deactivation, of these electrical paths/circuits automatically simply by depressing a button, switch, or the like and, similarly, releasing the button, switch, or the like. In this particular embodiment, a particular desired sequence is activated automatically by depressing on one side of the rocker and automatically deactivated in reverse order by releasing pressure on the same side of the rocker.

FIGS. 6A and 6B illustrate another embodiment of a TDM 600 comprising yet another alternative embodiment of a switch assembly 620 utilizing reed switches to achieve a safe activation sequence. Reed switches 624 and 625 may comprise glass tubes filled with inert gas and two contacts (624a & 624b and 625a & 625b) that can be pulled together or apart using a magnetic field. The magnetic field may be generated from, for example, a permanent magnet, a coil formed around the axis of the tube, or other means that generate magnetic fields. FIG. 6C, which illustrates the components of one of the two actuators (actuator 621) of switch assembly 620, illustrates one embodiment using permanent magnets 622 and 623 but a coil could also be used if it were provided power from a battery or power scavenging circuit, as described elsewhere in this disclosure.

TDM 600 comprises tip 601, shaft 602, and handle 603. FIG. 6A illustrates tip 601 that may be made up of a ceramic or other preferably non-conductive material. TDM 600 may comprise a cutting electrode set 633 and a coag electrode set 634, each of which may comprise one or more electrodes. Cutting electrode set 633 may comprise a plurality of lysing elements. In some embodiments, the plurality of lysing elements may comprise lysing segments. Such lysing elements may be positioned in between a plurality of protrusions positioned at the distal end of tip 601. Tip 601 further comprises a coagulation electrode set 634, which may comprise a plurality of coagulation electrodes positioned within an Energy Window. Electrode set 634 may, in some embodiments, terminate at a set of termini atop tip 601 in a chevron configuration.

FIG. 6C more particularly illustrates the elements of one actuator or button 621 of switch assembly 620. Actuator 621 may be configured for activating a CUT mode of TDM 600 and actuator 641 may be configured for activating a COAG mode of TDM 600. Buttons or actuators 621 and 641 of switch assembly 620 may each comprise two magnets, which may comprise permanent magnets, positioned underneath the respective buttons. With respect to each of the buttons, a first magnet 622 may correspond to the CUT electrode set 633 and second magnet 623 to the ESU CUT signal. Similarly, with respect to actuator 641, a first magnet (not shown) may correspond to the COAG electrode set 634 and a second magnet (not shown) may correspond to the ESU COAG signal.

RF source in lead 627 may supply both RF energies and the current for signal circuit activation. Magnets 622 and 623 may be oriented such that, as button 621 is depressed, the pole of magnet 622 to the CUT electrode set 633 (or, in the case of button 641, to the COAG electrode set 634) comes in proximity of the CUT electrode reed switch 624 (and its contacts 624a & 624b) before magnet to ESU CUT signal 623 comes close to CUT signal reed 625 (and its contacts 625a & 625b), thereby making the patient/electrode circuit first via the CUT electrode line 629. Configuring magnets 622 and 623 to perform this electrical coupling sequentially may be made possible by using magnets of different sizes, using magnets having different magnetic field strengths, or positioning one of the magnets closer to the patient/electrode circuit than the signal circuit, for example.

As the button continues to travel downward, the pole of magnet 623, which may be shorter/smaller than magnet 622, positioned further away from reed switch 625 than magnet 622 is from reed switch 624, and/or may have a lesser magnetic field strength than magnet 622, may actuate the CUT signal reed switch 625 and its contacts 625a & 625b, thereby completing the CUT signal circuit to the ESU via CUT signal path to ESU 628. When the button is released, magnet 623 opens reed switch 625, thereby signaling the ESU to stop delivering CUT energy. As the switch continues to travel upward, magnet 622 finally disconnects the CUT electrode from the active RF by disengaging contacts 624a & 624b of reed switch 624. Thus, the sequence of coupling of the two electrical paths referenced above may take place in reverse sequence upon releasing button 621 or otherwise deactivating a similar actuator.

The same or a similar sequence can be applied for COAG modes with a separate COAG electrode set or any other electrode modality. Thus, the sequence described above may also take place when COAG button/actuator 641 is depressed or otherwise actuated and, similarly, may take place in reverse upon deactivating COAG button/actuator 641.

In an additional embodiment, CUT button/actuator 641 may be a part of another structure affecting a COAG or another modality button/actuator in such a way that as one modality is pressed (CUT in this instance), the other magnet(s) move further away from their respective reed switches thus preventing two or more electrodes or electrode sets from carrying RF at the same time and/or with the same modality. Similarly, COAG button 641 may be part of another structure affecting a CUT or another modality button/actuator in such a way that as one modality is pressed (COAG in this instance), the other magnet(s) move further away from their respective reed switches to, again, prevent two distinct electrodes or electrode sets from carrying RF energy at the same time and/or with the same modality.

Figure 7A:
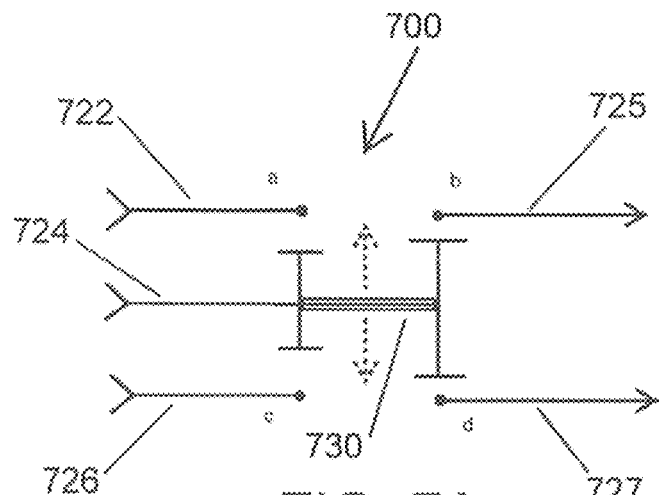
FIG. 7A is a schematic diagram illustrating the functionality of a switch assembly for use in an electrosurgical device according to some embodiments.

FIG. 7a is a schematic diagram of a switch 700 that may be used to sequentially couple one or more electrodes of a TDM or another electrosurgical device to one or more components of an electrosurgical generator unit (ESU) or another similar unit. The three lines on the left side of the diagram may represent an interface with various typical ports of an ESU. For example, line 722 may be coupled with a "Cut Signal" port of an ESU, line 724 may be configured to interface with an RF IN port, and line 726 may be configured to interface with a "Coag Signal" port. Switch 700 may operate, for example, by moving switch 700 in one of two directions (up and down from the perspective of the figure). By moving the switch 700 up, the structure of switch 700 may be configured to first electrically couple with contact "b," which may complete a circuit between one or more electrodes (preferable CUT electrodes) through line 725 and an RF IN port through line 724. Continued pressing or other movement of switch 700 in the same direction subsequently may result in electrically coupling with contact "a," which may send a cut signal to the ESU to turn on the cut mode.

Similarly, by moving the switch 700 in the opposite direction (down from the perspective of the figure), the structure of switch 700 may be configured to first electrically couple with contact "d," which may complete a circuit between one or more electrodes (preferable COAG electrodes) and an RF port through line 724. Continued pressing or other movement of switch 700 in the same direction may subsequently result in electrically coupling with contact "c," which may send a coag signal to the ESU to turn on the coag mode.

Switch 700 may be physically structured to accomplish making these sequential electrical connections automatically upon actuation. For example, in some embodiments, switch 700 may be configured to pivot or flex once contact is made on one side (e.g., with contact b or d) so as to subsequently make contact with a or c, respectively. This may be accomplished by making the contacts on one side of switch 700 longer, as illustrated in FIG. 7a.

Alternatively, or additionally, switch 700 may comprise one or more flexible materials or components configured to facilitate such sequential coupling. For example, in some embodiments, the central portion of switch 700 in between the opposite ends may comprise a spring 730, such as a moustache spring, as suggested by the triple-lined area within switch 700, which may be configured to allow for flexing of the spring as soon as an initial contact is made with contact b or d to then allow for subsequent coupling with contact a or c, respectively.

Figure 7B:
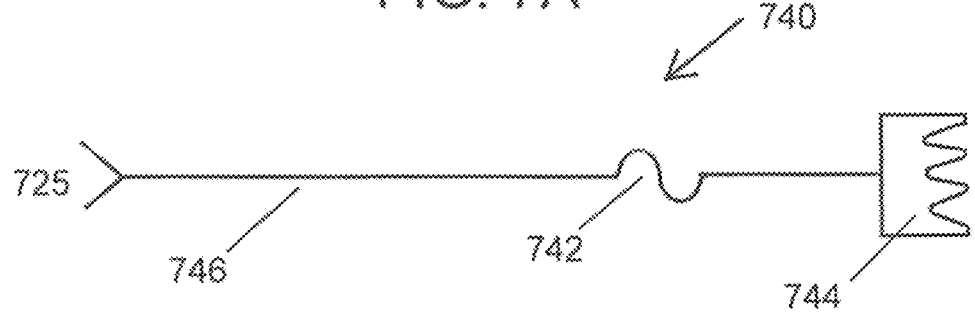
FIG. 7B is a schematic diagram of a TDM comprising a temperature sensor according to some embodiments.

FIG. 7b depicts an embodiment of an electrosurgical instrument, such as a TDM 740 comprising a thermal fuse 742. Thermal fuse 742 may be positioned in series with and may also be located in close proximity to, one or more of the electrodes within the tip 744 of TDM 740, such as one or more cutting electrodes, or in other locations within and/or about the tip 744 and/or shaft 746. If thermal fuse 742 opens, which may represent an indication that the blade temperature, other electrode temperature, or a temperature of another portion of tip 744 is exceeded, the device and/or one or more modes of the device may be rendered inoperable. For example, if thermal fuse 742 is coupled with a cut electrode, the cut mode may be rendered inoperable upon opening of thermal fuse 742. In other contemplated embodiments the thermal fuse 742 may be coupled with a coag electrode, such that the coag mode, or both the cut and coag modes, may be rendered inoperable upon actuation/opening of thermal fuse 742.

In the embodiment depicted in FIG. 7b, one or more of the electrodes may be positioned in series with thermal fuse 742. Thermal fuse 742 may then open when a particular threshold temperature is exceeded, thereby blocking the RF energy from reaching the cut blade or other electrode coupled in series with thermal fuse 742. In some embodiments, the threshold temperature may comprise a temperature at or near which one or more components of the device are likely to fail and/or at which operation of the device otherwise may become dangerous.

Figure 7C:
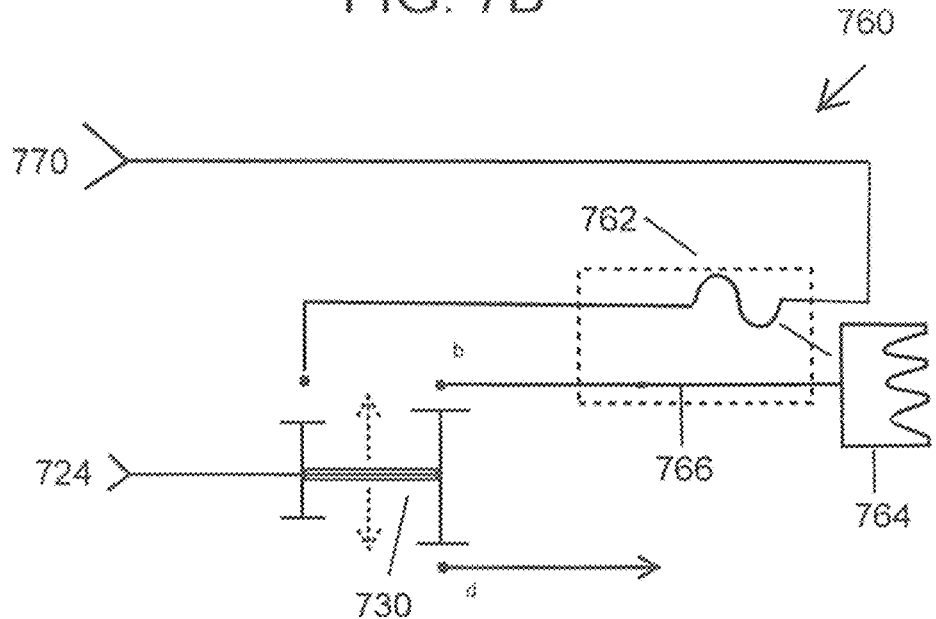
FIG. 7C is a schematic diagram illustrating the functional interaction between a switch assembly and a temperature sensor within a TDM according to some embodiments.

FIG. 7C depicts another embodiment of an electrosurgical device 760 comprising a thermal fuse 762 placed in series with a signal line (either a cut or coag signal, for example), rather than the actual electrode/RF line. Thus, in the depicted embodiment, thermal fuse 762 is positioned in series with signal line 770, which may also be positioned so as to make contact with a multi-stage, sequential switch, as described above, upon actuation. Thermal fuses 742 and 762 are both examples of means for temperature measurement and deactivation. This embodiment may be preferred for certain configurations because it may less susceptible to arcing upon actuation of fuse 762 due to its placement in series with a signal line to the ESU rather than an RF line. Thermal fuse 762 may be positioned in or near tip 764 of TDM 760 or, alternatively, may be positioned within shaft 766 of TDM 760.

Figure 8:
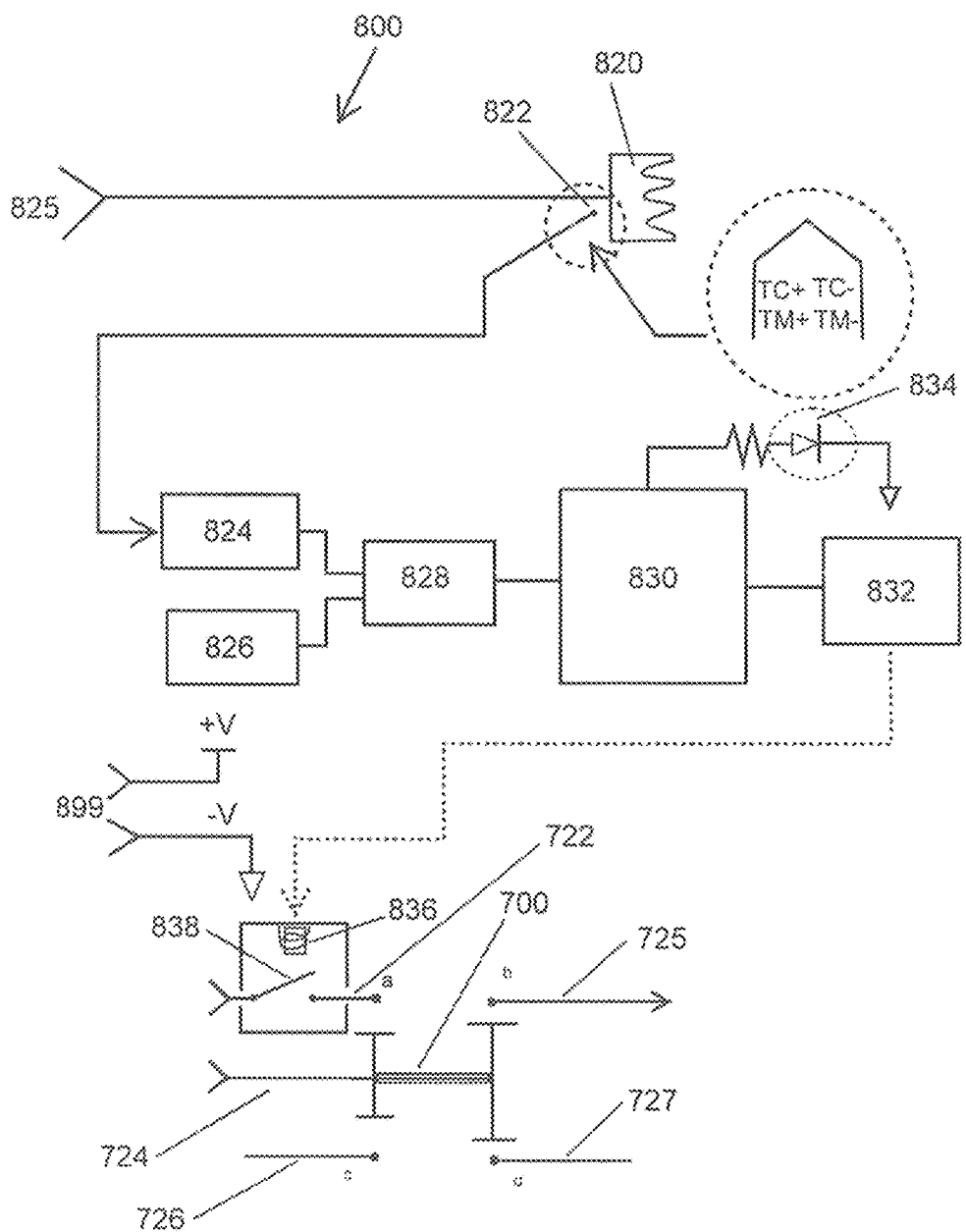
FIG. 8 is a schematic diagram illustrating the functionality of another embodiment of a temperature sensor and a switch assembly within a TDM.

FIG. 8 depicts a schematic diagram of an alternative means for temperature measurement and deactivation. In some embodiments, a temperature sensor 822 may be positioned in or near a tip 820 of a TDM or other electrosurgical device 800 comprising a signal or RF line 825. Temperature sensor 822 may comprise, for example, a thermistor or thermocouple. As shown in the exploded portion of FIG. 8, the thermistor or thermocouple may comprise a pair of wires ($TC^{+/-}$ or $TM^{+/-}$) which may be coupled to temperature measurement circuitry 824 to convert a microvolt or millivolt figure to, for example, a scaled output represented as millivolts per degrees Celsius.

In some embodiments, a limit signal 826 may be used as a reference signal, which may be scaled in the same units as the temperature measurement signal so that, for example, at 200 degrees C. the limit signal may be 200 mV=0.2V and may trigger a threshold action when the temp measurement output exceeds 0.2V. In other words, when the temperature measurement exceeds the limit signal 826, a comparator 828 may output a logic level signal to a microcontroller 830, which may receive an input signal from the comparator 828 and look for the presence of a signal indicative of a temperature having exceeded a threshold temperature. If the comparator 828 receives such a signal indicating that a temperature has exceeded a limit/set point, then microcontroller 830 may activate a relay 832, which may open a circuit, such as the same circuit that may be opened when a fuse is used in the cut or coag control signal path and/or an RF/electrode circuit.

In some embodiments, a visual indicator, such as an LED (Light Emitting Diode) 834 may be coupled with the microcontroller 830, which may be used to indicate that the device, or at least a portion of the device, has been rendered non-operational to the user due to excessive temperature. The LED 834 may be positioned, for example, on the handle of the device and may indicate to the surgeon that he or she should not keep pressing buttons and/or continue with the procedure.

The relay 832 is normally closed (meaning operational). However, when the microcontroller 830 receives a signal indicating that the threshold temperature has been reached or exceeded, the microcontroller 830 may actuate relay 832 to thereby open one or more circuits to cease operation of the device, or at least one or more elements of the device.

Temperature measurement circuitry 824 may be used, in some embodiments, to compare the actual tip temperature to the temperature limit. If the threshold temperature is exceeded, the relay may be configured to open the "cut signal" (and/or coag signal") to the ESU, thereby disabling RF energy. In some embodiments, the energy may be disabled permanently. In other embodiments, the energy may be disabled temporarily while the temperature drops and, optionally, while a fault-condition indicator 834 may alert the user. This circuitry may be powered 899 from a battery source or may be powered by scavenging electrical energy from the ESU, as described in greater detail below. This embodiment may be compatible with the TDM switches described in connection with previous embodiments.

The bottom portion of FIG. 8 illustrates how a signal, such as a relay signal from relay 832, may be used to open a circuit path to a signal circuit associated with a switch. As illustrated in this portion of the figure, in some embodiments, the circuit path may be opened using, for example, a solenoid 836, which may be configured to open a circuit upon receiving a signal from, for example, relay 832 by actuating a switch 838.

In some embodiments, the assembly used to break the circuit upon detection of an excessive temperature may be positioned in series with a signal line, such as line 722 that may be coupled with a "Cut Signal" or "Coag Signal" port of an ESU. A multi-stage, sequential switch, such as switch 700, as previously described.

In some embodiments, temperature sensor 822 may comprise a bimetallic strip that, when heated, bends and/or breaks contact with one or more RF electrodes and/or the CUT and/or COAG signal wire(s).

Still further embodiments may comprise a temperature sensor 822 that may comprise a phase change sensor. For example, some embodiments may be configured so as to sense a phase change associated with an epoxy or other insulation material, another bonding agent, or another material built into a portion of the TDM (preferably the tip). This phase change material may, in some embodiments, comprise a portion of the device that serves to keep the tip/device together, such as a bonding agent. The bonding agent or other such phase change material may be selected such that a melting temperature of the bonding agent/phase change material is close to a desired threshold temperature for operation of the device.

Upon detecting a phase change of the phase change material in the TDM or other electrosurgical device, the TDM may be configured to limit or modulate the energy delivery to one or more of the electrodes. In some embodiments, the TDM may be configured to completely terminate further delivery of RF and/or other energy to some, or all, of the electrodes upon detecting a phase change (likely from solid to liquid). Alternatively, upon detecting a phase change, or detecting that a phase change is likely to happen, a phase change sensor may be configured to reduce, or temporarily suspend, the delivery of RF and/or other energy to some, or all, of the electrodes. In some embodiments, the phase change sensor may be configured to, upon detecting a phase change, or detecting that a phase change is likely to happen, deliver a signal to, for example, the ESG, which may cause the ESG to terminate or modulate, the energy delivery. In some embodiments, the phase change sensor may be configured to, upon detecting a phase change, or detecting that a phase change is likely to happen, sever and/or open one or more of the circuit paths referenced above.

In some embodiments, a switch assembly may be configured to provide multiple bipolar electrode sets with separate modes of power delivery. FIG. 9a depicts an example of a TDM 900 configured to allow for switching between distinct bipolar electrode sets. TDM 900 comprises a handle 902, a tip 910, a shaft 905 extending between handle 902 and tip 910, a 3-pinned plug 920, and a monopolar return connector 921. The 3-pinned plug 920 may be configured to be positioned into an ESG/ESU receptacle having corresponding pin receptacles. Handle 902 may receive source/signal wires from plug 920 and monopolar return connector 921. In some embodiments, handle 902 may also house a switching assembly for switching between cutting and coagulation RF waveforms in a plurality of distinct electrode sets, which is another example of a switching means, as described above.

FIG. 9b is a close-up view of tip 910, which may be made up of a ceramic or other preferably non-conductive material. Tip 910 may comprise a CUT electrode set 914 comprising a plurality of bipolar lysing elements. Such elements may be positioned in between a plurality of protrusions positioned at the distal end of tip 910. Tip 910 further comprises a COAG electrode set 912, which may be positioned within an Energy Window on an upper surface of tip 910. Electrodes 912 terminate at a plurality of bipolar termini in a chevron configuration.

Figure 9C:
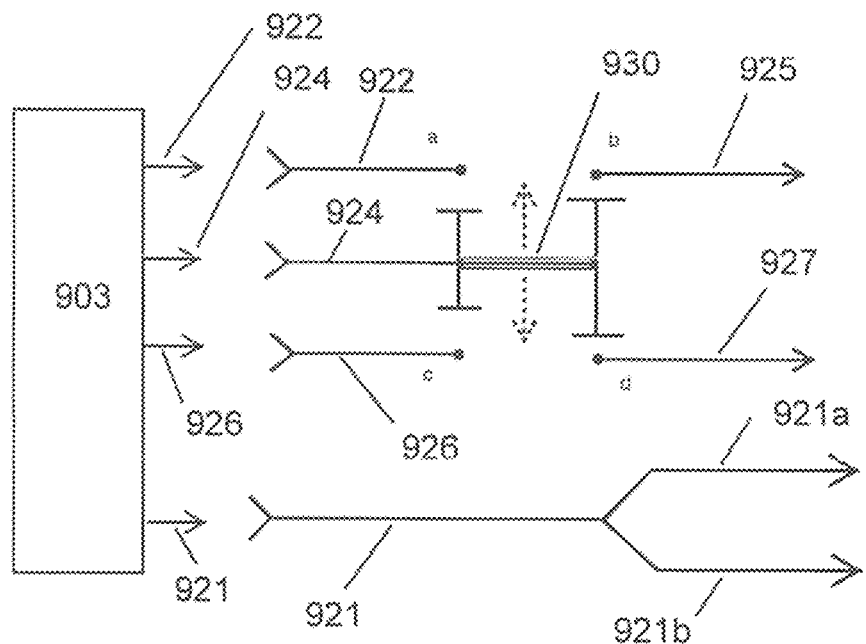
FIG. 9C is a schematic diagram illustrating the functionality of a switch assembly and various related components that may be used in connection with the bipolar TDM of FIG. 9A.

As also shown in FIG. 9b, each electrode in electrode sets 914 and 912 comes in a pair with a corresponding electrode of an opposite polarity, as labeled (+ and −) in the figure. The positive (+) electrodes may receive electrosurgical energy from an ESU via a switch assembly, such as the switch assembly 51 illustrated schematically in FIG. 9c. The negative (−) electrodes may receive electrosurgical energy from an ESU monopolar return via monopolar return connector 921.

The negative conductor of the CUT electrode set 914 and the negative conductor of the COAG electrode set 912 may be connected together and electrically coupled to monopolar return connector 921 at 921a and 921b, respectively. Monopolar return connector may be electrically coupled to a monopolar return of the ESU 903.

The positive conductors of the CUT electrode set 914 may be connected to contact b (FIG. 9c) of switch 930. The positive conductors of the COAG electrode set 912 may be electrically coupled to contact d (FIG. 9c) of switch 930.

Switch 930 may be operated in a similar manner to the monopolar embodiments described above. Thus, when the switch is enabled for CUT mode, RF will travel to the positive CUT electrodes, pass through tissue and return through the negative electrode and back to the ESU 903 via monopolar return connector 921. Similarly, when the switch is enabled for COAG mode, RF will travel to the positive COAG electrodes, pass through tissue and return through the negative electrode and back to the ESU via monopolar return connector 921.

More particularly, the top three lines on the left side of the diagram may represent an interface with various typical ports of an ESU 903. For example, line 922 may be coupled with a "Cut Signal" port 903a of ESU 903, line 924 may be configured to interface with an RF IN port 903b, and line 926 may be configured to interface with a "Coag Signal" port 903c. Switch 930 may operate, for example, operate by moving switch 930 in one of two directions (up and down from the perspective of the figure). By moving the switch 930 up, the structure of switch 930 may be configured to first electrically couple with contact "b," which may complete a circuit between one or more electrodes (e.g., CUT electrodes) through line 925 and an RF IN port through line 924. Continued pressing or other movement of switch 930 in the same direction subsequently may result in electrically coupling with contact "a," which may send a cut signal to the ESU 903 to turn on the cut mode.

Similarly, by moving the switch 930 in the opposite direction (down from the perspective of the figure), the structure of switch 930 may be configured to first electrically couple with contact "d," which may complete a circuit between one or more electrodes (e.g., COAG electrodes) through line 927 and an RF port through line 924. Continued pressing or other movement of switch 930 in the same direction may subsequently result in electrically coupling with contact "c," which may send a coag signal to the ESU to turn on the coag mode.

Switch 930 may be physically structured to accomplish making these sequential electrical connections automatically upon actuation. For example, in some embodiments, switch 930 may be configured to pivot or flex once contact is made on one side (e.g., with contact b or d) so as to subsequently make contact with a or c, respectively. This may be accomplished by making the contacts on one side of switch 930 longer, as illustrated in FIG. 9c.

Figures 9D, 9E:
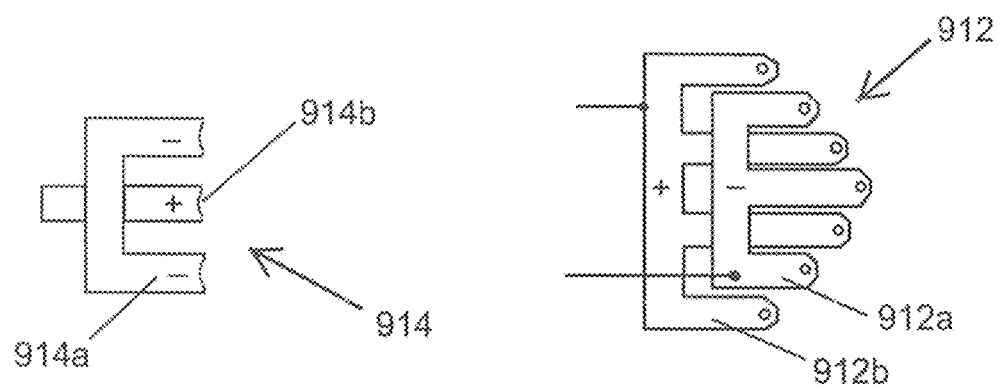
FIG. 9D illustrates the CUT electrodes of the bipolar TDM of FIG. 9A shown removed from the tip of the TDM.
FIG. 9E illustrates the COAG electrodes of the bipolar TDM of FIG. 9A shown removed from the tip of the TDM.

FIG. 9d illustrates an example of a possible configuration of CUT electrode set 914, shown removed from the remainder of TDM 900. The electrodes in set 914 may be arranged such that RF preferentially passes between the activated pair. Thus, positive electrode 914b may be positioned to extend between opposing ends of negative electrode 914a. In some embodiments, a dielectric material, such as, for example, a polyimide such as Kapton®, polytetrafluoroethylene, or a suitable ceramic material.

FIG. 9e illustrates an example of a possible configuration of COAG electrode set 912, shown removed from the remainder of TDM 900. The electrodes in set 912 may be arranged such that RF preferentially passes between the activated pair. Thus, positive electrode 912b may be positioned such that various positive electrode termini extend adjacent to corresponding termini of negative electrode 912a. As with CUT electrode set 914, a dielectric material may be used to separate the positive and negative electrodes of COAG electrode set 912.

FIG. 10a illustrates another embodiment of a surgical tool 1000 that may be specifically configured for minimally invasive surgery, such as laparoscopic, endoscopic, or keyhole surgery, for example. Tool 1000 comprises a shaft 1020, a handle 1022, and a trigger 1024. A spot coagulator 1032 extends along shaft 1020. Spot coagulator 1032 may extend adjacent to an exterior surface of shaft 1020. Alternatively, as depicted in the figure, spot coagulator 1032 may be positioned within a lumen of shaft 1020 and therefore extend within shaft 1020. Spot coagulator 1032 may comprise a monopolar spot coagulator or, alternatively, may comprise a split tip at spot coagulator tip 1026 and comprise a bipolar spot coagulator. In some embodiments, a water jet 1033 may be positioned to extend adjacent to an exterior surface of shaft 1020 or, alternatively, as depicted in the figure, water jet 1022 may be positioned within a lumen of shaft 1020 and therefore extend within shaft 1020. Water jet 1022 may comprise a port at a distal end of shaft 1020 to allow for selectively applying a stream of water or another liquid during a surgical procedure.

In some embodiments, shaft 1020 may comprise a Teflon-coated rod made of stainless steel or a similar, preferably biocompatible, material. Shaft 1020 may comprise one or more lumens to allow for various wires, lines, or other items to extend therethrough.

A lysing tip 1046 may be coupled to the distal end of tool 1000. In some embodiments, lysing tip 1046 may be coupled to the remainder of tool 1000 by using coupling member 1044. This may allow for use of pre-existing tools, such as laparoscopes, to include various elements for delivery of electrosurgical energy, as described elsewhere herein.

Lysing tip 1046 may comprise one or more lysing elements 1028 configured for delivery of CUT or BLEND electrosurgical energy, as best illustrated in FIG. 10b. In some embodiments, each lysing element 1028 may be positioned between adjacent protrusions formed at the distal end of tip 1046. Because spot coagulator 1032 may be configured to deliver a different type of electrosurgical energy and/or may be configured to deliver such energy at distinct times, surgical tool 1000 may further comprise a switch assembly 1050 configured to switch between operation of spot coagulator 1032 and lysing element 1028.

Spot coagulator 1032 may be retractable and/or extendable along lysing tip 1046. For example, in the depicted embodiment, spot coagulator 1032 may be retracted and/or extended using a spot coagulator moving means, which may comprise toggle 1036. Toggle 1036 may further comprise a toggle base 1038 to facilitate movement of toggle 1036, and thereby facilitate movement of spot coagulator 1032, thereon. In alternative embodiments, various rails, grooves, tracks, ratchets, cables, arms, lines, etc. may be used as spot coagulator moving means. Toggle 1036 may be positioned directly on tool 1000 or, alternatively, may be positioned on a rod, shaft, or other coupling means extending adjacent to tool 1000, to allow for selective advancement and retraction of the spot coagulator 1032.

Alternatively, or additionally, a spot coagulator moving means comprising a spot coagulator handle 1040 may be provided. Handle 1040 may comprise a hook, loop, groove, or other feature configured to facilitate use by a finger and/or hand of a surgeon.

A pivoting member 1030 may be coupled with trigger 1024 to allow for pivoting coupling member 1044 and/or lysing tip 1046. In some embodiments, a shaped laparoscope tip 1042 may be coupled to the distal end of shaft 1020. Tip 1042 may comprise an angle configured to interface with similar angled proximal edge of coupling member 1044. As shown in the figure, in some embodiments, the angle at which the proximal edge of coupling member 1044 or, alternatively, a proximal edge of lysing tip 1046, extends relative to a plane perpendicular to the direction in which shaft 1020 extends may be a mirror image of the distal surface of shaft 1020. This angle may be selected to facilitate a desired amount of angulation of lysing tip 1046. In some embodiments, coupling member 1044 may allow for retrofitting a lysing tip 1046 to an existing laparoscope or other surgical instrument.

In some embodiments, one or more of the components discussed above may be coupled with a robotic arm to allow for performing remote surgical procedures. For example, in some embodiments, an assembly comprising a lysing tip, such as lysing tip 1046, a spot coagulator, such as spot coagulator 1032, and/or a switch assembly, such as switch assembly 1050, may be coupled with a robotic arm.

Thus, FIG. 10c depicts an embodiment of a system 1060 for performing robotic surgery using an assembly comprising a spot coagulator, switch assembly, and lysing tip. System 1060 may comprise a lysing tip 1062 that may, as described elsewhere herein, comprise a plurality of protrusions with one or more lysing elements positioned therebetween. Lysing tip 1062 may, in some embodiments, be part of an assembly including one or more other components, such as a shaft 1064, which in some embodiments may comprise a flexible shaft suitable for placement in an endoscope or other similar device. A spot coagulator may be positioned inside of or otherwise adjacent to shaft 1064 and/or lysing tip 1062, as described above.

In such embodiments, a switch assembly, as described above, may be provided to allow for selective switching between various electrosurgical modes, as described above, for delivery to a lysing element of lysing tip 1062 and/or a spot coagulator. This assembly may be selectively coupled to a robotic arm 1070 such that the alternate means for delivery of electrosurgical energy may be coupled with one or more robotic surgery components to allow a surgeon to perform a surgical procedure with the assembly remotely and/or indirectly. In other embodiments, the assembly may be configured to be integrally coupled with, or otherwise non-selectively coupled with, one or more robotic surgery components. In such embodiments, it may not be necessary to configure the assembly with a handle and/or shaft. In other words, in some embodiments, the assembly may comprise only a tip with a lysing element and spot coagulator.

In some embodiments, the robotic surgery system 1060 may comprise one or more motors, such as a screw-drive motor, gear motor, hydraulic motors, etc. In some embodiments, the robotic surgery system 1060 may comprise worm gearheads, video cameras, motor control circuits, monitors, remote control devices, illumination sources, tactile interface, etc. In the embodiment depicted in FIG. 10c, robotic arm 1070 comprises a plurality of arm segments 1072 with corresponding joints 1074 positioned therebetween. A primary joint 1075 may be positioned to support and articulate together each of the arm segments 1072 and smaller joints 1074. Primary joint 1075 has a primary arm segment 1077 that extends therefrom. Finer movements of the robotic arm may then be accomplished using one or more of the smaller joints 1076.

A stand 1080 may also be provided to support the various robotic arms. In some embodiments, stand 1080 may also be configured to support a monitor 1082 and/or other display, input, or control components, such as a control element 1084. In some embodiments, control element 1084 may comprise a hand control toggle. In other embodiments, control element 1084 may comprise a keyboard, mouse, touchscreen display, virtual reality system, control pad, or the like. Monitor 1082 and/or control element 1084 may be communicatively coupled with a central processing unit 1086.

The invention claimed is:

1. An electrosurgical device, comprising:
   a first electrode set configured to deliver CUT radiofrequency energy;
   a second electrode set configured to deliver COAG radiofrequency energy, wherein the second electrode set is electrically isolated from the first electrode set; and
   a rocker switch assembly configured to allow for selection between at least three modes to facilitate operation of the electrosurgical device in the at least three modes, the at least three modes comprising:
      a first, neutral mode, in which the electrosurgical device is configured such that no radiofrequency energy is delivered to either the first electrode set or the second electrode set;
      a second, CUT mode, in which the electrosurgical device is configured such that the CUT radiofrequency energy may be delivered to the first electrode set through the rocker switch assembly without delivering the CUT radiofrequency energy to the second electrode set; and
      a third, COAG mode, in which the electrosurgical device is configured such that the COAG radiofrequency energy may be delivered to the second electrode set through the rocker switch assembly without delivering the COAG radiofrequency energy to the first electrode set, wherein the rocker switch assembly is further configured to allow for selection of a first sub-mode of the CUT mode in which an electrical path between the first electrode set and a radiofrequency source is closed but an electrical path associated with a signal circuit for activating the CUT radiofrequency energy is open, wherein the rocker switch assembly is configured to automatically transition from the first sub-mode of the CUT mode to a final configuration of the CUT mode in which the electrical path associated with the signal circuit for activating the CUT radiofrequency energy is closed upon actuation of the rocker switch assembly, wherein the rocker switch assembly is further configured to allow for selection of a first sub-mode of the COAG mode in which an electrical path between the second electrode set and the radiofrequency source is closed but an electrical path associated with a signal circuit for activating the COAG radiofrequency energy is open, wherein the rocker switch assembly is configured to automatically transition from the first sub-mode of the COAG mode to a final configuration of the COAG mode in which the electrical path associated with the signal circuit for activating the COAG radiofrequency energy is closed upon actuation of the rocker switch assembly, wherein the rocker switch assembly is further configured to at least one of open the electrical path between the second electrode set and the radiofrequency source and increase a clearance distance between adjacent contacts associated with the second electrode set upon transitioning between the neutral mode and the CUT mode, and wherein the rocker switch assembly is further configured to at least one of open the electrical path between the first electrode set and the radiofrequency source and increase a clearance distance between adjacent contacts associated with the first electrode set upon transitioning between the neutral mode and the COAG mode.

2. The electrosurgical device of claim 1, wherein the electrosurgical device is configured such that a blended waveform comprising both CUT and COAG radiofrequency is delivered from the first electrode set in the second, CUT mode.

3. The electrosurgical device of claim 1, wherein the first electrode set comprises a plurality of electrodes.

4. The electrosurgical device of claim 3, further comprising a tip comprising a plurality of protrusions and a plurality of lysing elements positioned in between the plurality of protrusions, wherein the plurality of electrodes at least partially define the plurality of lysing elements.

5. The electrosurgical device of claim 1, further comprising a tip comprising a plurality of protrusions and a plurality of lysing segments positioned in between the plurality of protrusions, wherein the first electrode set at least partially defines the plurality of lysing segments.

6. The electrosurgical device of claim 1, wherein the second electrode set comprises a plurality of electrodes.

7. The electrosurgical device of claim 6, further comprising a tip comprising at least one energy window positioned on the tip, wherein the plurality of electrodes at least partially define the at least one energy window.

8. The electrosurgical device of claim 1, wherein the rocker switch assembly is further configured such that, in the first mode, the electrical path between the first electrode set and the radiofrequency source is open and the electrical path between the second electrode set and the radiofrequency source is open.

9. The electrosurgical device of claim 1, wherein the rocker switch assembly is further configured such that, in the first mode, the electrical path between the first electrode set and the radiofrequency source is closed, the electrical path between the second electrode set and the radiofrequency source is closed, the electrical path associated with the signal circuit for activating the CUT radiofrequency energy is open, and the electrical path associated with the signal circuit for activating the COAG radiofrequency energy is open.

10. The electrosurgical device of claim 9, wherein the rocker switch assembly is configured to open the electrical path between the first electrode set and the radiofrequency source upon transitioning from the first mode to the third mode, and wherein the rocker switch assembly is further configured to open the electrical path between the second electrode set and the radiofrequency source upon transitioning from the first mode to the second mode.

11. The electrosurgical device of claim 1, wherein the electrosurgical device comprises a monopolar electrosurgical device.

12. The electrosurgical device of claim 1, wherein the adjacent contacts associated with the first and second electrode sets comprise:
   a movable signal circuit contact on each of two opposing sides of the rocker switch assembly;
   a fixed signal circuit contact on each of the two opposing sides of the rocker switch assembly;
   a movable radiofrequency source contact on each of the two opposing sides of the rocker switch assembly; and
   a fixed radiofrequency source contact on each of the two opposing sides of the rocker switch assembly, wherein each of the fixed signal circuit contacts and each of the fixed radiofrequency source contacts is positioned in an least substantially planar position relative to each other.

13. An electrosurgical device, comprising:
- at least one first electrode;
- at least one second electrode electrically insulated from the at least one first electrode; and
- means for switching between distinct radiofrequency waveforms, wherein the switching means is configured to close an electrical path to the at least one first electrode and activate a signal circuit associated with a first radiofrequency waveform to send the first radiofrequency waveform to the at least one first electrode, wherein the switching means is configured to separately close an electrical path to the at least one second electrode and activate a signal circuit associated with a second radiofrequency waveform to send the second radiofrequency waveform to the at least one second electrode, wherein the switching means is configured to both open the electrical path between the at least one first electrode and the first radiofrequency waveform and increase a clearance distance between adjacent contacts associated with the at least one first electrode upon transitioning from the first radiofrequency waveform to the second radiofrequency waveform, and wherein the switching means is further configured to both open the electrical path between the at least one second electrode and the second radiofrequency waveform and increase a clearance distance between adjacent contacts associated with the at least one second electrode upon transitioning from the second radiofrequency waveform to the first radiofrequency waveform.

14. The electrosurgical device of claim 13, wherein the at least one first electrode comprises a first plurality of electrodes, and wherein the at least one second electrode comprises a second plurality of electrodes.

15. The electrosurgical device of claim 14, wherein the electrosurgical device comprises a bipolar electrosurgical device, wherein the first plurality of electrodes comprises positive and negative electrodes, and wherein the second plurality of electrodes comprises positive and negative electrodes.

16. The electrosurgical device of claim 13, further comprising a temperature sensor configured to, upon sensing a threshold temperature, at least one of activate a visual indicator and open at least one of the electrical paths to at least one of the at least one first electrode and the at least one second electrode.

17. The electrosurgical device of claim 16, wherein the temperature sensor is configured to, upon sensing the threshold temperature, open an electrical path to at least one of the signal circuit associated with the first radiofrequency waveform and the signal circuit associated with the second radiofrequency waveform.

18. The electrosurgical device of claim 17, wherein the temperature sensor comprises a thermal fuse positioned in series with at least one of the electrical path to the signal circuit associated with the first radiofrequency waveform and the electrical path to the signal circuit associated with the second radiofrequency waveform.

19. The electrosurgical device of claim 17, wherein the temperature sensor comprises a thermal fuse positioned in series with at least one of the electrical path to the at least one first electrode and the electrical path to the at least one second electrode.

20. The electrosurgical device of claim 17, wherein the temperature sensor comprises:
- temperature measurement circuitry; and
- at least one of a thermistor and a thermocouple coupled to the temperature measurement circuitry, wherein the temperature sensor is configured to convert a temperature to at least one of a voltage and a current output using a scale associating the at least one of a voltage and a current output with a temperature.

21. The electrosurgical device of claim 13, wherein the means for switching between distinct radiofrequency waveforms is configured to close the electrical path to the at least one first electrode before activating the signal circuit associated with the first radiofrequency waveform, and wherein the switching means is further configured to separately close the electrical path to the at least one second electrode before activating the signal circuit associated with the second radiofrequency waveform.

22. The electrosurgical device of claim 13, wherein the means for switching between distinct radiofrequency waveforms comprises a rocker switch.

23. The electrosurgical device of claim 22, wherein the rocker switch is configured to sequentially close the electrical path to the at least one first electrode before activating the signal circuit associated with the first radiofrequency waveform upon depressing a first end of the rocker switch, and wherein the rocker switch is configured to sequentially close the electrical path to the at least one second electrode before activating the signal circuit associated with the second radiofrequency waveform upon depressing a second end of the rocker switch.

\* \* \* \* \*